(12) United States Patent
Popov et al.

(10) Patent No.: US 7,728,128 B2
(45) Date of Patent: Jun. 1, 2010

(54) DIBENZO[C,H][1,5]NAPHTHYRIDINES AND THEIR USE AS DNA PROBES

(75) Inventors: Andreï Popov, Voreppe (FR); David Grierson, Vancouver (CA); Jean-Claude Florent, Gif sur Yvette (FR)

(73) Assignees: Institut National de la Sante et de la Recherche Medicate (INSERM), Paris (FR); Institut Curie, Paris (FR); Centre National de la Recherche Scientifique (C.N.R.S.), Paris (FR); Commissariat a l'Energie Atomique, Paris (FR)

( * ) Notice: Subject to any disclaimer, the term of this patent is extended or adjusted under 35 U.S.C. 154(b) by 0 days.

(21) Appl. No.: 12/280,715

(22) PCT Filed: Feb. 15, 2007

(86) PCT No.: PCT/IB2007/000360

§ 371 (c)(1),
(2), (4) Date: Feb. 24, 2009

(87) PCT Pub. No.: WO2007/096728

PCT Pub. Date: Aug. 30, 2007

(65) Prior Publication Data

US 2009/0246772 A1 Oct. 1, 2009

(30) Foreign Application Priority Data

Feb. 27, 2006 (EP) .................................. 06290322

(51) Int. Cl.
C07D 293/01 (2006.01)
C12Q 1/68 (2006.01)
C07H 21/02 (2006.01)
C07H 21/04 (2006.01)
C07H 19/04 (2006.01)
B01L 3/00 (2006.01)

(52) U.S. Cl. .................. 544/1; 544/3; 435/6; 536/23.1; 536/24.3; 536/26.6; 422/61

(58) Field of Classification Search .................. 435/6; 536/23.1, 26.6, 24.3; 422/61; 544/1, 3
See application file for complete search history.

(56) References Cited

OTHER PUBLICATIONS

Bisagni E. et al., "A Convenient Way to Dibenzo[c,h]-1,5-naphthyridines (11-aza-benzo[c] phenanthridines)", Tetrahedron, Elsevier Science Publishers, Amsterdam, NL, vol. 52, No. 31, Jul. 29, 1996, pp. 10427-10440.
Antonini I, et al., "N4-(omega-Aminoalkyl)-1-[(omega-aminoalkyl)amino]-4-acridinecarboxamides: Novel, Potent, Cytotoxic, and DNA-binding Agents", Journal of Medicinal Chemistry, vol. 43, No. 25, Dec. 14, 2000, pp. (4801-4805).

*Primary Examiner*—Jezia Riley
(74) *Attorney, Agent, or Firm*—B. Aaron Schulman; Terry L. Wright; Stites & Harbison PLLC

(57) ABSTRACT

The present invention concerns novel dibenzo[c,h][1,5]naphthyridine of formula (I) and their use as DNA probes, as well as the methods for marking DNA using the same.

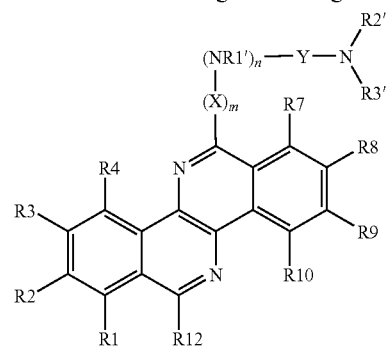

14 Claims, 6 Drawing Sheets

A

Figure 1:
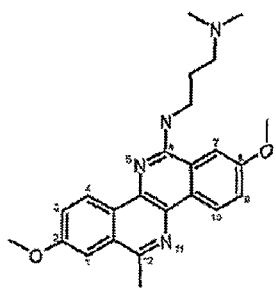
Figure 1:
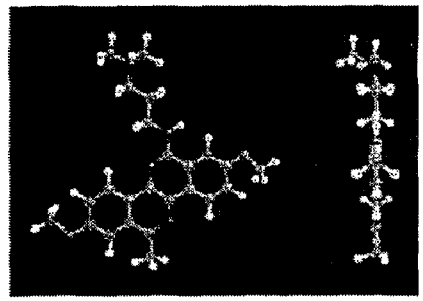
Figure 1:
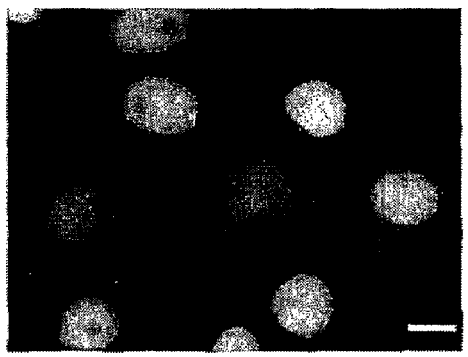
Figure 1:
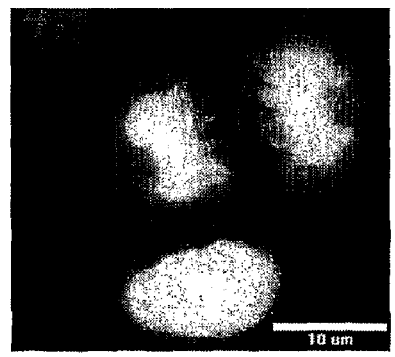
Figure 1:
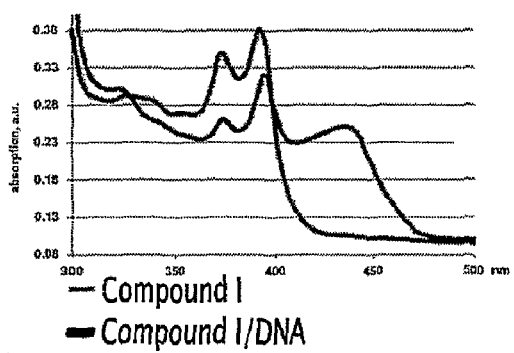
Figure 1:

N'-(2,8-Dimethoxy-12-methyl-dibenzo[c,h][1,5]naphthyridin-6-yl)-N,N-dimethyl-propane-1,3-diamine

B

C

D

E

— Compound I
— Compound I/DNA

F a  b  c  d e  f  g

DIBENZO[C,H][1,5]NAPHTHYRIDINES AND THEIR USE AS DNA PROBES

Nucleic acid-binding fluorescent compounds are widely used for DNA visualization, purification and quantification. Among the most frequent applications are gel electrophoresis, flow cytometry, real-time quantification of the product during PCR, DNA revelation in indirect epifluorescence on fixed cells (staining of nuclei and mitotic chromosomes) and mutagenesis (Haugland, R. P. (ed.) 2002, *Nucleic Acid Detection and Genomics Technology*, chapter 8, Ninth ed. Molecular Probes, Inc., Eugene, Oreg.). Since the 1950s, a variety of DNA and RNA non-covalently binding probes have been discovered. They can be classified according to their molecular structure, the class of nucleic acids they bind to, and their mode of binding. The most frequently used fluorescent dyes (Hoechst, DAPI, Ethidium bromide) bind strongly and preferentially to dsDNA, while others (such as the SYTO dyes) stain all types of nucleic acids depending on the conditions (Haughland et al., supra). These properties correlate well with the molecular structures of these reagents. For example, ethidium bromide and propidium iodide intercalate into dsDNA (Lerman, L. S., 1961, *J Mol Biol*, 3, 18-3), whereas the cationic dyes Hoechst and DAPI interact with the minor groove of dsDNA, showing a net preference for dA/dT rich sequences (Kopka, M. L., et al., 1985, *Proc Nat Acad Sci USA*, 82, 1376-1380; Kubista, M. et al., 1987, *Biochemistry*, 26, 4545-4553). Interestingly, certain DNA markers show both types of binding, depending on their concentration relative to nucleic acids (Zipper, H. et al., 2004, *Nucleic Acids Res*, 32, e103). An original mode of binding was proposed for the TOTO dye which is thought to intercalate between bases of the same strand of ssDNA (Rye, H. S. et al., 1995, *Nucleic Acids Res*, 23, 1215-1222).

Today, experimentation with live cells has gained widespread interest, primarily due to the development of technologies to film proteins, nucleic acids and organelles labelled with fluorescent small molecules or different versions of GFP (Zhang, J. et al., 2002, *Nat Rev Mol Cell Biol*, 3, 906-918; Shav-Tal Y. et al., 2004, *Nat Rev Mol Cell Biol*, 5, 855-861; Zink D. et al., 2003, *Methods*, 29, 42-50). These applications are dependent on the possibility to illuminate cells for relatively long periods of time without inflicting damage. However, most of the traditional cell-permeant DNA-binding dyes used in cell biology (DAPI, Hoechst 33342 or 33258) require illumination with light in the ultraviolet (UV, 200-400 nm) part of the spectrum. At these wavelengths extensive photodamage occurs, due, amongst other things, to formation of free radicals, and to cross-links in DNA and/or DNA-associated proteins (Alexander, P. et al., 1962, *Nature*, 194, 882-883; Pfeifer, G. P. et al., 2005, *Mutat Res*, 571, 19-31). These events are followed by failure to replicate DNA and/or failure to enter (Palitti, F., 2004, *Cytogenet Genome Res*, 104, 95-99) and accomplish mitosis. This ultimately leads to cell cycle arrest and death (Kulms, D. et al., 2002, *Skin Pharmacol Appl Skin Physiol*, 15, 342-347). Both ethidium bromide and propidium iodide can be excited at longer than UV wavelengths. However, propidium bromide does not penetrate into cells, and ethidium bromide intercalates into the DNA of living mammalian cells to only a very limited extent (Tramier, M., et al., 2000, *Biophys J*, 78, 2614-2627). There is thus a need to develop new fluorescent DNA probes for live-cell video microscopy and cell sorting which are: (i) cell membrane-permeant and non-toxic; (ii) excited at longer than UV wavelengths; and/or (iii) stable over long periods of illumination.

The present inventors have now discovered dibenzo[c,h][1,5]naphthyridine derivatives which display dsDNA-binding cell-permeant fluorescent dye properties. They are very attractive reagents for in vivo experiments to visualize DNA.

According to a first object, the present invention concerns derivatives of formula (I).

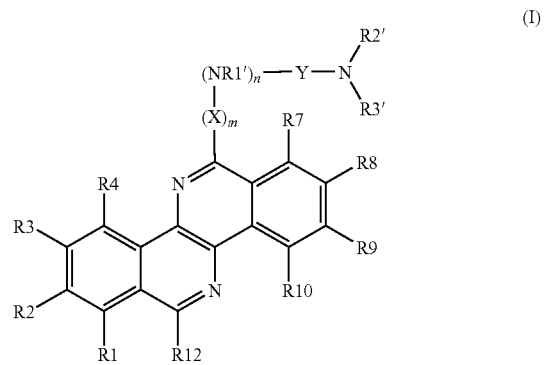

wherein

R1, R3, R4, R7, R9 and R10 are identical or different and independently chosen from H; Alkyl optionally substituted by one or more —NRR', —OH, OAlkyl, CF$_3$; a halogen atom; —NRR'; —OH; OAlkyl; CF$_3$; preferably R1=R3=R4=R7=R9=R10=H;

R2=H; OAlkyl; O(C2-C10)Alkyl wherein (C2-C10)Alkyl is substituted by one or more —NRR', —OH, OAlkyl, CF$_3$; a halogen atom; —NRR'; —OH; OAlkyl; CF$_3$; preferably H or —OAlkyl; more preferably OAlkyl;

R1'=H; Alkyl or (C2-C10)Alkyl wherein (C2-C10)Alkyl is substituted by one or more —NRR', —OH, OAlkyl, CF$_3$; a halogen atom; —NRR'; —OH; OAlkyl; CF$_3$; preferably H;

n=0 or 1; preferably, n=1;

X=linear Alkyl;

m=0 or 1; preferably, m=0;

Y=linear Alkyl; preferably, linear Alkyl comprising 3 or more carbon atoms;

R2' and R3', identical or different, are independently chosen from H; Alkyl or (C2-C10)Alkyl wherein (C2-C10)Alkyl is substituted by one or more —OH, —NRR', —OAlkyl, CF$_3$; preferably, R2' and R3' are not simultaneously H; more preferably, R2' and R3', identical or different, are independently chosen from H; Alkyl optionally substituted by one or more OH; most preferably R2'=R3'=Alkyl;

R8=H; OAlkyl; O(C2-C10)Alkyl wherein (C2-C10)Alkyl is substituted by one or more —NRR', —OH, OAlkyl, CF$_3$; a halogen atom; —NRR'; —OH; OAlkyl; CF$_3$; preferably H, —OAlkyl; more preferably OAlkyl; most preferably OMethyl;

R12=H; Alkyl optionally substituted by one or more —NRR', —OH, OAlkyl, CF$_3$,

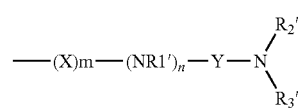

wherein X, R1', R2', R3', Y, m, n are defined as above; preferably, R12=H, Alkyl or

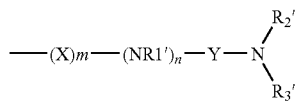

wherein X, R1', R2', R3', Y, m, n are defined as above; more preferably, R12=Alkyl;

R, R', identical or different, represent independently H, Alkyl or (C2-C10)Alkyl wherein (C2-C10)Alkyl is substituted by one or more —NRR', —OH, OAlkyl, $CF_3$; preferably, R, R' identical or different are H or Alkyl;

or their acceptable salts, hydrates, or hydrated salts, or the polymorphic crystalline structures of these compounds or their optical isomers, racemates, diastereomers or enantiomers, with the exception of compounds wherein:

R1=R3=R4=R7=R9=R10=H, m=0, n=1, R1'=H, R2'=R3'=Methyl, R2, R8 represent independently H or OMethyl, R12=H or Methyl and Y=—$(CH_2)_2$— or —$(CH_2)_3$—.

More particularly, the compounds of the invention are selected from:

N'-Dibenzo[c,h][1,5]naphthyridin-6-ylmethyl-N,N-diethyl-propane-1,3-diamine (Compound 2), 2-[2-(Dibenzo[c,h][1,5]naphthyridin-6-ylamino)-ethylamino]-ethanol (Compound 3), N'-dibenzo[c,h][1,5]naphthyridin-6-yl-methyl-N,N-dimethyl-ethane-1,2-diamine (Compound 5), N'-dibenzo[c,h][1,5]naphthyridin-6-yl-methyl-N,N-dimethyl-propane-1,3-diamine (Compound 6), N'-dibenzo[c,h][1,5]naphthyridin-6-yl-methylamino-2-methyl-propane-1,3-diol (Compound 7), N'-(2-methoxy-12-methyl-dibenzo[c,h][1,5]naphthyridin-6-yl)-N,N-dimethyl-propane-1,3-diamine (Compound 8), N6,N12-bis-(2-dimethylamino-ethyl)-2-methoxy-dibenzo[c,h][1,5]naphthyridin-6,12-diamine (Compound 9), N6,N12-bis-(3-dimethylamino-propyl)-2-methoxy-dibenzo[c,h][1,5]naphthyridine-6,12-diamine (Compound 10), N,N'-bis-(3-dimethylaminopropyl)-2,8-dimethoxy-dibenzo[c,h][1,5]naphthyridin-6,12-diamine (Compound 11), N,N'-bis-(3-dimethylamino-ethyl)-2,8-dimethoxy-dibenzo[c,h][1,5]naphthyridin-6,12-diamine (Compound 14), or their acceptable salts, hydrates, or hydrated salts, or the polymorphic crystalline structures of these compounds or their optical isomers, racemates, diastereomers or enantiomers.

As used hereabove or hereafter:

"Alkyl" means an aliphatic hydrocarbon group which may be straight or branched having 1 to 20 carbon atoms in the chain. Preferred alkyl groups have 1 to 12 carbon atoms in the chain. Branched means that one or more lower alkyl groups such as methyl, ethyl or propyl are attached to a linear alkyl chain. Exemplary alkyl groups include methyl, ethyl, n-propyl, i-propyl, n-butyl, t-butyl, n-pentyl, 3-pentyl, octyl, nonyl, decyl.

"Halogen atom" refers to fluorine, chlorine, bromine or iodine atom; preferably fluorine and chlorine atom.

"Alkyl" refers also to the corresponding "alkylene", such as methylene, which is formed by the removal of two hydrogen atoms.

As used herein, the term "acceptable" refers to those compounds, materials, compositions, or dosage forms which are, within the scope of sound medical judgment, suitable for contact with the tissues of human beings and animals without excessive toxicity, irritation, allergic response, or other problem complications commensurate with a reasonable benefit/risk ratio.

As used herein, "acceptable salts" refer to derivatives of the disclosed compounds wherein the parent compound is modified by making acid or base salts thereof. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, tartaric, citric, methanesulfonic, benzenesulfonic, glucoronic, glutamic, benzoic, salicylic, toluenesulfonic, oxalic, fumaric, maleic, and the like. Further addition salts include ammonium salts such as tromethamine, meglumine, epolamine, etc., metal salts such as sodium, potassium, calcium, zinc or magnesium.

The acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Generally, non-aqueous media like ether, ethyl acetate, ethanol, isopropanol, or acetonitrile are preferred. Lists of suitable salts are found in *Remington's Pharmaceutical Sciences,* 17$^{th}$ ed., Mack Publishing Company, Easton, Pa., 1985, p. 1418, the disclosure of which is hereby incorporated by reference.

The compounds of the general formula (I) having geometrical and stereoisomers are also a part of the invention.

According to a further object, the present invention is also concerned with the process of preparation of the compounds of formula (I).

The compounds and process of the present invention may be prepared in a number of ways well known to those skilled in the art. The compounds can be synthesized, for example, by application or adaptation of the methods described below, or variations thereon as appreciated by the skilled artisan. The appropriate modifications and substitutions will be readily apparent and well known or readily obtainable from the scientific literature to those skilled in the art.

In particular, such methods can be found in R. C. Larock, *Comprehensive Organic Transformations, VCH publishers,* 1989.

More precisely, the compounds of the invention may be prepared by application or adaptation of the methods disclosed by Bisagni et al (1996) Tetrahedron 53, 10427-10440.

It will be appreciated that the compounds of the present invention may contain one or more asymmetrically substituted carbon atoms, and may be isolated in optically active or racemic forms. Thus, all chiral, diastereomeric, racemic forms and all geometric isomeric forms of a structure are intended, unless the specific stereochemistry or isomeric form is specifically indicated. It is well known in the art how to prepare and isolate such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

Compounds of the present invention may be prepared by a variety of synthetic routes. The reagents and starting materials are commercially available, or readily synthesized by well-known techniques by one of ordinary skill in the arts. All substituents, unless otherwise indicated, are as previously defined.

In the reactions described hereinafter, it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in *Protective Groups in Organic Chemistry*, John Wiley and Sons, 1991; J. F. W. McOmie in *Protective Groups in Organic Chemistry*, Plenum Press, 1973.

Some reactions may be carried out in the presence of a base. There is no particular restriction on the nature of the base to be used in this reaction, and any base conventionally used in reactions of this type may equally be used here, provided that it has no adverse effect on other parts of the molecule. Examples of suitable bases include: sodium hydroxide, potassium carbonate, triethylamine, alkali metal hydrides, such as sodium hydride and potassium hydride; alkyllithium compounds, such as methyllithium and butyllithium; and alkali metal alkoxides, such as sodium methoxide and sodium ethoxide.

Usually, reactions are carried out in a suitable solvent. A variety of solvents may be used, provided that it has no adverse effect on the reaction or on the reagents involved. Examples of suitable solvents include: hydrocarbons, which may be aromatic, aliphatic or cycloaliphatic hydrocarbons, such as hexane, cyclohexane, benzene, toluene and xylene; amides, such as dimethylformamide; alcohols such as ethanol and methanol and ethers, such as diethyl ether and tetrahydrofuran.

The reactions can take place over a wide range of temperatures. In general, the inventors find it convenient to carry out the reaction at a temperature of from 0° C. to 150° C. (more preferably from about room temperature to 100° C.). The time required for the reaction may also vary widely, depending on many factors, notably the reaction temperature and the nature of the reagents. However, provided that the reaction is effected under the preferred conditions outlined above, a period of from 3 hours to 20 hours will usually suffice.

The compounds thus prepared may be recovered from the reaction mixture by conventional means. For example, the compounds may be recovered by distilling off the solvent from the reaction mixture or, if necessary after distilling off the solvent from the reaction mixture, pouring the residue into water followed by extraction with a water-immiscible organic solvent and distilling off the solvent from the extract. Additionally, the product can, if desired, be further purified by various well known techniques, such as recrystallization, reprecipitation or the various chromatography techniques, notably column chromatography or preparative thin layer chromatography.

According to an aspect of the process of the invention, compounds of formula (I) where m=0 and n=1 may be obtained from reacting corresponding compounds of formula (II):

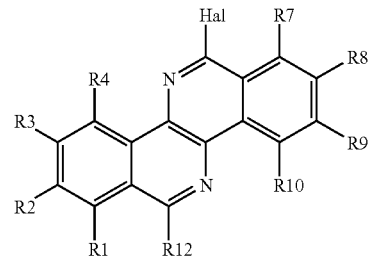

with corresponding compounds of formula (II'):

NHR1'-Y—NR2'R3' (II')

wherein R1-R12, R1'-R3' and Y are defined as in formula (I) and Hal represents a halogen atom, such as chlore.

According to a further aspect of the process of the invention, compounds of formula (I) where m=1 may be obtained from corresponding compounds of formula (III):

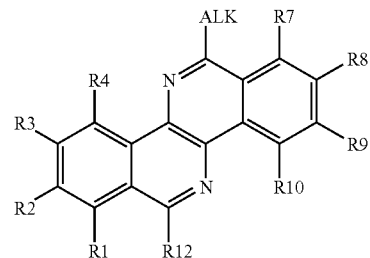

by carrying out an oxidation followed by a reductive amination with the corresponding compound of formula (III'):

(NHR1')$_n$-Y—NR2'R3' (III')

wherein R1-R12, R1'-R3', n and Y are defined as in formula (I) and ALK represents a alkyl group.

Generally, the oxidation step is performed with SeO2 or equivalent.

The reductive amination may be conducted as a one-pot or following intermediate isolation of the compound (III")

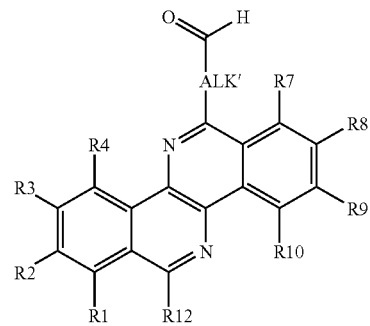

wherein R1-R12 are defined as in formula (I) and ALK' represents the corresponding precursor of ALK.

Compounds of formula (II), (II'), (III) and (III') may obtained by application or adaptation of the methods taught in Bisagni et al. and/or may be commercially available.

Further, the process of the invention may also comprise the additional step of isolating the compound of formula (I). This can be done by the skilled person by any of the known conventional means, such as the recovery methods described above.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double or triple or more stranded helix. Double-stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA round, inter alia, in linear (e.g., restriction fragments) or circular DNA molecules, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

According to a further object, the present invention is also concerned with the use of a compound of formula (I):

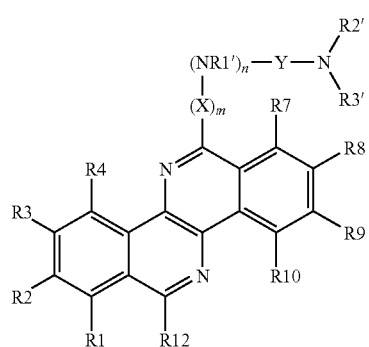

wherein:

R1, R3, R4, R7, R9 and R10 are identical or different and independently chosen from H; Alkyl optionally substituted by one or more —NRR', —OH, OAlkyl, $CF_3$; a halogen atom; —NRR'; —OH; OAlkyl; $CF_3$; preferably R1=R3=R4=R7=R9=R10=H;

R2=H; OAlkyl; O(C2-C10)Alkyl wherein (C2-C10)Alkyl is substituted by one or more —NRR', —OH, OAlkyl, $CF_3$; a halogen atom; —NRR'; —OH; OAlkyl; $CF_3$; preferably H or —OAlkyl; more preferably OAlkyl;

R1'=H; Alkyl or (C2-C10)Alkyl wherein (C2-C10)Alkyl is substituted by one or more —NRR', —OH, OAlkyl, $CF_3$; a halogen atom; —NRR'; —OH; OAlkyl; $CF_3$; preferably H;

n=0 or 1; preferably, n=1;

X=linear Alkyl;

m=0 or 1; preferably, m=0;

Y=linear Alkyl; preferably, linear Alkyl comprising 3 or more carbon atoms;

R2' and R3', identical or different, are independently chosen from H; Alkyl or (C2-C10)Alkyl wherein (C2-C10)Alkyl is substituted by one or more —OH, —NRR', —OAlkyl, $CF_3$; preferably, R2' and R3' are not simultaneously H; more preferably, R2' and R3', identical or different, are independently chosen from H; Alkyl optionally substituted by one or more OH; most preferably R2'=R3'=Alkyl;

R8=H; OAlkyl; O(C2-C10)Alkyl wherein (C2-C10)Alkyl is substituted by one or more —NRR', —OH, OAlkyl, $CF_3$; a halogen atom; —NRR'; —OH; OAlkyl; $CF_3$; preferably H, —OAlkyl; more preferably OAlkyl; most preferably OMethyl;

R12=H; Alkyl optionally substituted by one or more —NRR', —OH, OAlkyl, $CF_3$,

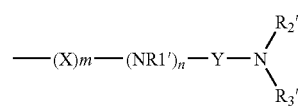

wherein X, R1', R2', R3', Y, m, n are defined as above; preferably, R12=H, Alkyl or

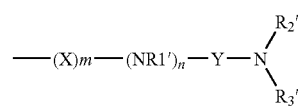

wherein X, R1', R2', R3', Y, m, n are defined as above; more preferably, R12=Alkyl;

R, R', identical or different, represent independently H, Alkyl or (C2-C10)Alkyl wherein (C2-C10)Alkyl is substituted by one or more —NRR', —OH, OAlkyl, $CF_3$;

or their acceptable salts, hydrates, or hydrated salts, or the polymorphic crystalline structures of these compounds or their optical isomers, racemates, diastereomers or enantiomers, as a DNA probe.

Compounds for the use of the invention may be chosen from:

N'-(2,8-dimethoxy-12-methyl-dibenzo[c,h][1,5]naphthyridin-6-yl)-N,N-dimethyl-propane-1,3-diamine (Compound 1), N'-Dibenzo[c,h][1,5]naphthyridin-6-ylmethyl-N,N-diethyl-propane-1,3-diamine (Compound 2), N'-2-[2-(Dibenzo[c,h][1,5]naphthyridin-6-ylamino)-ethylamino]-ethanol (Compound 3), N'-Dibenzo[c,h][1,5]naphthyridin-6-yl-N,N-dimethyl-ethane-1,3-diamine (Compound 4), N'-Dibenzo[c,h][1,5]naphthyridin-6-ylmethyl-N,N-dimethyl-ethane-1,3-diamine (Compound 5), N'-dibenzo[c,h][1,5]naphthyridin-6-ylmethyl-N,N-dimethyl-propane-1,2-diamine (Compound 6), N'-dibenzo[c,h][1,5]naphthyridin-6-yl-methylamino-2-methyl-propane-1,3-diol (Compound 7), N'-(2-methoxy-12-methyl-dibenzo[c,h][1,5]naphthyridin-6-yl)-N,N-dimethyl-propane-1,3-diamine (Compound 8), N6,N12-bis-(2-dimethylamino-ethyl)-2-methoxy-dibenzo[c,h][1,5]naphthyridin-6,12-diamine (Compound 9), N6,N12-bis-(3-dimethylamino-propyl)-2-methoxy-dibenzo[c,h][1,5]naphthyridine-6,12-diamine (Compound 10), N,N'-bis-(3-dimethylaminopropyl)-2,8-dimethoxy-dibenzo[c,h][1,5]naphthyridin-6,12-diamine (Compound 11), N'-(2,8-dimethoxy-12-methyl-dibenzo[c,h][1,5]naphthyridin-6-yl)-N,N-dimethyl-ethane-1,3-diamine (Compound 12), N'-(2,8-dimethoxy-dibenzo[c,h][1,5]naphthyridin-6-yl)-N,N-dimethyl-ethane-1,3-diamine (Compound 13), N,N'-bis-(3-dimethylamino-ethyl)-2,8-dimethoxy-dibenzo[c,h][1,5]naphthyridin-6,12-diamine (Compound 14), or their acceptable salts, hydrates, or hydrated salts, or the polymorphic crystalline structures of these compounds or their optical isomers, racemates, diastereomers or enantiomers.

According to a further object, the present invention is also concerned with the use of a compound of formula (I):

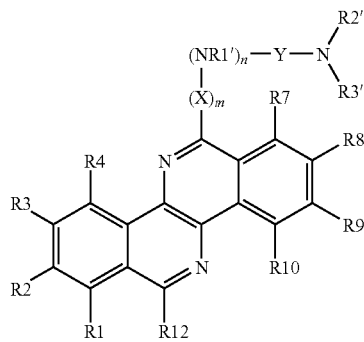

(I)

wherein:

R1, R3, R4, R7, R9 and R10 are identical or different and independently chosen from H; Alkyl optionally substituted by one or more —NRR', —OH, OAlkyl, $CF_3$; a halogen atom; —NRR'; —OH; OAlkyl; $CF_3$; preferably R1=R3=R4=R7=R9=R10=H;

R2H; OAlkyl; O(C2-C10)Alkyl wherein (C2-C10)Alkyl is substituted by one or more —NRR', —OH, OAlkyl, $CF_3$; a halogen atom; —NRR'; —OH; OAlkyl; $CF_3$; preferably H or —OAlkyl; more preferably OAlkyl;

R1'=H; Alkyl or (C2-C10)Alkyl wherein (C2-C10)Alkyl is substituted by one or more —NRR', —OH, OAlkyl, $CF_3$; a halogen atom; —NRR'; —OH; OAlkyl; $CF_3$; preferably H;

n=0 or 1; preferably, n=1;

X=linear Alkyl;

m=0 or 1; preferably, m=0;

Y=linear Alkyl; preferably, linear Alkyl comprising 3 or more carbon atoms;

R2' and R3', identical or different, are independently chosen from H; Alkyl or (C2-C10)Alkyl wherein (C2-C10)Alkyl is substituted by one or more —OH, —NRR', —OAlkyl, $CF_3$; preferably, R2' and R3' are not simultaneously H; more preferably, R2' and R3', identical or different, are independently chosen from H; Alkyl optionally substituted by one or more OH; most preferably R2'=R3'=Alkyl;

R8=H; OAlkyl; O(C2-C10)Alkyl wherein (C2-C10)Alkyl is substituted by one or more —NRR', —OH, OAlkyl, $CF_3$; a halogen atom; —NRR'; —OH; OAlkyl; $CF_3$; preferably H, —OAlkyl; more preferably OAlkyl; most preferably OMethyl;

R12=H; Alkyl optionally substituted by one or more —NRR', —OH, OAlkyl, $CF_3$,

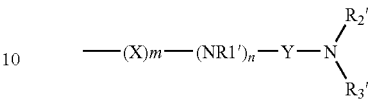

wherein X, R1', R2', R3', Y, m, n are defined as above; preferably, R12=H, Alkyl or

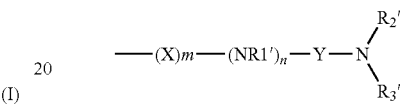

wherein X, R1', R2', R3', Y, m, n are defined as above; more preferably, R12=Alkyl;

R, R', identical or different, represent independently H, Alkyl or (C2-C10)Alkyl wherein (C2-C10)Alkyl is substituted by one or more —NRR', —OH, OAlkyl, $CF_3$;

or their acceptable salts, hydrates, or hydrated salts, or the polymorphic crystalline structures of these compounds or their optical isomers, racemates, diastereomers or enantiomers, for the preparation of a DNA probe.

Compounds for the use of the invention may be chosen from:

N'-(2,8-dimethoxy-12-methyl-dibenzo[c,h][1,5]naphthyridin-6-yl)-N,N-dimethyl-propane-1,3-diamine (Compound I), N'-Dibenzo[c,h][1,5]naphthyridin-6-ylmethyl-N,N-diethyl-propane-1,3-diamine (Compound 2), N'-2-[2-(Dibenzo[c,h][1,5]naphthyridin-6-ylamino)-ethylamino]-ethanol (Compound 3), N'-Dibenzo[c,h][1,5]naphthyridin-6-yl-N,N-dimethyl-ethane-1,3-diamine (Compound 4), N'-Dibenzo[c,h][1,5]naphthyridin-6-ylmethyl-N,N-dimethyl-ethane-1,3-diamine (Compound 5), N'-dibenzo[c,h][1,5]naphthyridin-6-ylmethyl-N,N-dimethyl-propane-1,2-diamine (Compound 6), N'-dibenzo[c,h][1,5]naphthyridin-6-yl-methylamino-2-methyl-propane-1,3-diol (Compound 7), N'-(2-methoxy-12-methyl-dibenzo[c,h][1,5]naphthyridin-6-yl)-N,N-dimethyl-propane-1,3-diamine (Compound 8), N6,N12-bis-(2-dimethylamino-ethyl)-2-methoxy-dibenzo[c,h][1,5]naphthyridin-6,12-diamine (Compound 9), N6,N12-bis-(3-dimethylamino-propyl)-2-methoxy-dibenzo[c,h][1,5]naphthyridine-6,12-diamine (Compound 10), N,N'-bis-(3-dimethylaminopropyl)-2,8-dimethoxy-dibenzo[c,h][1,5]naphthyridin-6,12-diamine (Compound 11), N'-(2,8-dimethoxy-12-methyl-dibenzo[c,h][1,5]naphthyridin-6-yl)-N,N-dimethyl-ethane-1,3-diamine (Compound 12), N'-(2,8-dimethoxy-dibenzo[c,h][1,5]naphthyridin-6-yl)-N,N-dimethyl-ethane-1,3-diamine (Compound 13), N,N'-bis-(3-dimethylamino-ethyl)-2,8-dimethoxy-dibenzo[c,h][1,5]naphthyridin-6,12-diamine (Compound 14), or their acceptable salts, hydrates, or hydrated salts, or the polymorphic crystalline structures of these compounds or their optical isomers, racemates, diastereomers or enantiomers.

According to a preferred aspect, the compound of formula (I) is a selective DNA probe.

According to a further aspect, the compound of formula (I) is a DNA fluorescent staining probe, more preferably photoactivable probe.

The invention also further relates to the use of a compound of formula (I):

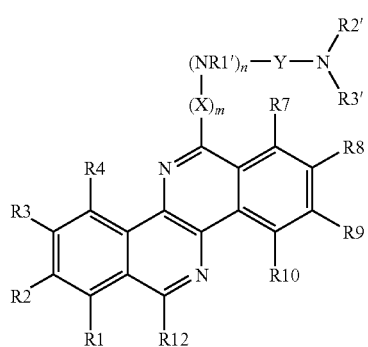

wherein:

R1, R3, R4, R7, R9 and R10 are identical or different and independently chosen from H; Alkyl optionally substituted by one or more —NRR', —OH, OAlkyl, $CF_3$; a halogen atom; —NRR'; —OH; OAlkyl; $CF_3$; preferably R1=R3=R4=R7=R9=R10=H;

R2=H; OAlkyl; O(C2-C10)Alkyl wherein (C2-C10)Alkyl is substituted by one or more —NRR', —OH, OAlkyl, $CF_3$; a halogen atom; —NRR'; —OH; OAlkyl; $CF_3$; preferably H or —OAlkyl; more preferably OAlkyl;

R1'=H; Alkyl or (C2-C10)Alkyl wherein (C2-C10)Alkyl is substituted by one or more —NRR', —OH, OAlkyl, $CF_3$; a halogen atom; —NRR'; —OH; OAlkyl; $CF_3$; preferably H;

n=0 or 1; preferably, n=1;

X=linear Alkyl;

m=0 or 1; preferably, m=0;

Y=linear Alkyl; preferably, linear Alkyl comprising 3 or more carbon atoms;

R2' and R3', identical or different, are independently chosen from H; Alkyl or (C2-C10)Alkyl wherein (C2-C10)Alkyl is substituted by one or more —OH, —NRR', —OAlkyl, $CF_3$; preferably, R2' and R3' are not simultaneously H; more preferably, R2' and R3', identical or different, are independently chosen from H; Alkyl optionally substituted by one or more OH; most preferably R2'=R3'=Alkyl;

R8=H; OAlkyl; O(C2-C10)Alkyl wherein (C2-C10)Alkyl is substituted by one or more —NRR', —OH, OAlkyl, $CF_3$; a halogen atom; —NRR'; —OH; OAlkyl; $CF_3$; preferably H, —OAlkyl; more preferably OAlkyl; most preferably OMethyl;

R12=H; Alkyl optionally substituted by one or more —NRR', —OH, OAlkyl, $CF_3$,

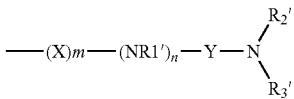

wherein X, R1', R2', R3', Y, m, n are defined as above; preferably, R12=H, Alkyl or

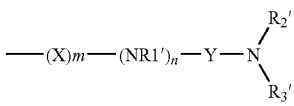

wherein X, R1', R2', R3', Y, m, n are defined as above; more preferably, R12=Alkyl;

R, R', identical or different, represent independently H, Alkyl or (C2-C10)Alkyl wherein (C2-C10)Alkyl is substituted by one or more —NRR', —OH, OAlkyl, $CF_3$;

or their acceptable salts, hydrates, or hydrated salts, or the polymorphic crystalline structures of these compounds or their optical isomers, racemates, diastereomers or enantiomers, for detecting DNA in a test sample.

Indeed, the derivatives of the invention are selective DNA dyes. In particular, they show selectivity for DNA over RNA, or other cellular constituents such as mitochondria or proteins.

These DNA dyes are capable of forming a non-covalent complex with DNA and demonstrate an increased fluorescent signal after formation of the DNA-dye complex.

Thus, the invention also concerns a complex wherein at least one derivative of formula (I) is non-covalently associated with a DNA molecule.

The DNA molecule may be a double-stranded DNA (dsDNA) or a DNA helix of higher strandness, or a mixed DNA-RNA helix. Preferably, the DNA molecule is a dsDNA.

The compounds of the invention are membrane-permeable. Therefore, they may be used to probe DNA in cellulo, for instance for probing DNA in a tissue, cell, organelle, or to probe DNA ex cellulo, for instance for probing DNA in a cell lysate or in an amplification mixture. Accordingly, the DNA molecule may be nuclear genomic DNA e.g. in the form of a chromosome, a plasmid, a circular DNA molecule, an oligonucleotide, or fragments thereof, e.g. a restriction fragment.

According to an embodiment, the test sample is a biological sample, i.e. the DNA is of biological origin.

The term "sample" as used herein refers to any material, including any biological derived material, which may contain nucleic acids, in particular DNA. The sample may also include diluents, buffers, detergents, and contaminating species, such as proteins or cell or tissue debris that may be found mixed with the target DNA molecule. The sample may be prepared using methods well known in the art for isolating DNA for in vitro and semi-solid or solution based detection assays, or for in vivo and/or intracellular DNA detection in live or fixed cells.

Examples of biological samples include urine, sera, blood, plasma, cerebrospinal fluid, saliva, tear fluid, tissues such as obtainable by biopsy, mucus or cells or a microorganism. In particular, the sample may be a cell, optionally cultured, dissolved or in suspension in a liquid material such as a buffer, extracting solution, a solvent and the like. Cells include without limitation prokaryotic cells such as bacteria, yeast, fungi, and eukaryotic cells such as plant and animal cells that include primary cell cultures and immortalized cell lines.

The sample may also be an immobilized tissue or cell, for instance on a solid or semi-solid support. In particular, the compounds of formula (I) may be used as DNA dyes in cells fixed and treated with classical histochemical or cytochemical procedures. Exemplary solid supports include an array (in particular a microarray), a microtitre plate, a blotting membrane such as a nitrocellulose membrane, a bead or a slide. A semi-solid support may be for instance a polymeric gel, or agar, agarose, methylcellulose which may be used for culturing or suspending cells.

The sample may further be a cell lysate, optionally separated from cell debris, which may have been dissolved or suspended in a liquid material such as a buffer, extracting solution, a solvent and the like.

The DNA may also be a synthetic DNA. A synthetic DNA has been prepared artificially for instance by reverse-transcription (RT) of a RNA matrix, RT-PCR, or by PCR of a DNA matrix or any other nucleic acid amplification method known in the art. Accordingly, the test sample may include material in which DNA has been added for instance a PCR reaction mixture and the likes, a gel such as (poly)acrylamide or agarose gel which are typically used as an electrophoretic matrix, or a buffer solution containing the DNA. The DNA molecule to be detected, hence the derivative/DNA complex, may thus be present in an electrophoretic matrix or polymeric gel.

Accordingly, the test sample may be selected from the group consisting of urine, sera, blood, plasma, cerebrospinal fluid, saliva, tear fluid, mucus, tissues optionally fixed or immobilized, eukaryotic or prokaryotic cells optionally fixed or immobilized, a cell lysate, a microorganism, an electrophoretic matrix or polymeric gel, or a buffered solution such as a PCR reaction mixture.

The invention also concerns an in vivo and/or in vitro method for detecting DNA in a test sample, which comprises the steps consisting of:

a) contacting a test sample with a derivative of formula (I)

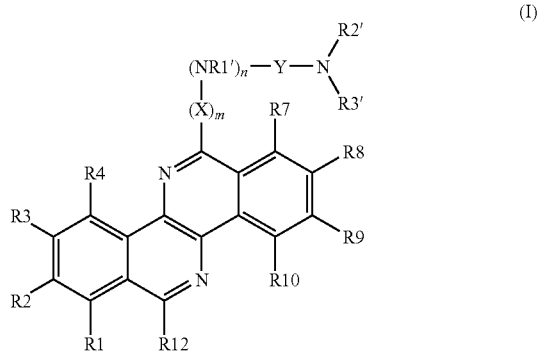

wherein:

R1, R3, R4, R7, R9 and R10 are identical or different and independently chosen from H; Alkyl optionally substituted by one or more —NRR', —OH, OAlkyl, CF$_3$; a halogen atom; —NRR'; —OH; OAlkyl; CF$_3$; preferably R1=R3=R4=R7=R9=R10=H;

R2=H; OAlkyl; O(C2-C10)Alkyl wherein (C2-C10)Alkyl is substituted by one or more —NRR', —OH, OAlkyl, CF$_3$; a halogen atom; —NRR'; —OH; OAlkyl; CF$_3$; preferably H or —OAlkyl; more preferably OAlkyl;

R1'=H; Alkyl or (C2-C10)Alkyl wherein (C2-C10)Alkyl is substituted by one or more —NRR', —OH, OAlkyl, CF$_3$; a halogen atom; —NRR'; —OH; OAlkyl; CF$_3$; preferably H;

n=0 or 1; preferably, n=1;

X=linear Alkyl;

m=0 or 1; preferably, m=0;

Y=linear Alkyl; preferably, linear Alkyl comprising 3 or more carbon atoms;

R2' and R3', identical or different, are independently chosen from H; Alkyl or (C2-C10)Alkyl wherein (C2-C10)Alkyl is substituted by one or more —OH, —NRR', —OAlkyl, CF$_3$; preferably, R2' and R3' are not simultaneously H; more preferably, R2' and R3', identical or different, are independently chosen from H; Alkyl optionally substituted by one or more OH; most preferably R2'=R3'=Alkyl;

R8=H; OAlkyl; O(C2-C10)Alkyl wherein (C2-C10)Alkyl is substituted by one or more —NRR', —OH, OAlkyl, CF$_3$; a halogen atom; —NRR'; —OH; OAlkyl; CF$_3$; preferably H, —OAlkyl; more preferably OAlkyl; most preferably OMethyl;

R12=H; Alkyl optionally substituted by one or more —NRR', —OH, OAlkyl, CF$_3$,

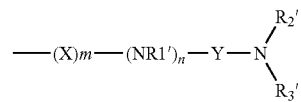

wherein X, R1', R2', R3', Y, m, n are defined as above; preferably, R12=H, Alkyl or

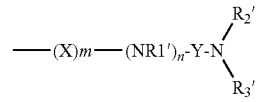

wherein X, R1', R2', R3', Y, m, n are defined as above; more preferably, R12=Alkyl;

R, R', identical or different, represent independently H, Alkyl or (C2-C10)Alkyl wherein (C2-C10)Alkyl is substituted by one or more —NRR', —OH, OAlkyl, CF$_3$;

or their acceptable salts, hydrates, or hydrated salts, or the polymorphic crystalline structures of these compounds or their optical isomers, racemates, diastereomers or enantiomers, b) incubating the mixture resulting from the contacting of the test sample and derivative of formula (I), for a time and under conditions sufficient for the derivative of formula (I) to form a complex with a DNA likely to be present in the test sample;

c) illuminating the mixture with an appropriate wavelength and observing the light emitted by the illuminated mixture, whereby the DNA is detected.

The derivative of formula (I) may be contacted with the test sample in the form of a "labelling solution". Such a labelling solution typically comprises a derivative of formula (I) dissolved in a suitable "labelling solvent" which may be an aqueous solvent such as water, a buffer solution such as phosphate buffered saline (PBS), or an organic solvent such as dimethylsulfoxide (DMSO), dimethylformamide (DMF), methanol, ethanol or acetonitrile, optionally in the presence of detergents and/or stabilizer. Examples of suitable detergents include SDS, Tween 20, CHAPS, or Triton-X. The detergent is typically present in an aqueous solution at a concentration from about 0.1% to about 0.5% (w/v).

According to a further object, the present invention is also concerned with a DNA labelling solution which comprises a compound of formula (I)

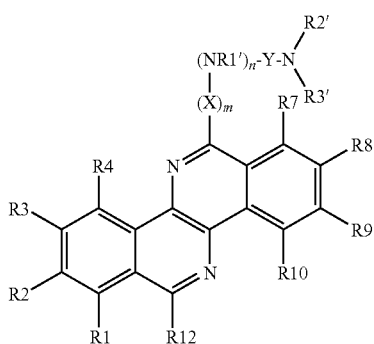

wherein:

R1, R3, R4, R7, R9 and R10 are identical or different and independently chosen from H; Alkyl optionally substituted by one or more —NRR', —OH, OAlkyl, CF$_3$; a halogen atom; —NRR'; —OH; OAlkyl; CF$_3$; preferably R1=R3=R4=R7=R9=R10=H;

R2=H; OAlkyl; O(C2-C10)Alkyl wherein (C2-C10)Alkyl is substituted by one or more —NRR', —OH, OAlkyl, CF$_3$; a halogen atom; —NRR'; —OH; OAlkyl; CF$_3$; preferably H or —OAlkyl; more preferably OAlkyl;

R1'=H; Alkyl or (C2-C10)Alkyl wherein (C2-C10)Alkyl is substituted by one or more —NRR', —OH, OAlkyl, CF$_3$; a halogen atom; —NRR'; —OH; OAlkyl; CF$_3$; preferably H;

n=0 or 1; preferably, n=1;

X=linear Alkyl;

m=0 or 1; preferably, m=0;

Y=linear Alkyl; preferably, linear Alkyl comprising 3 or more carbon atoms;

R2' and R3', identical or different, are independently chosen from H; Alkyl or (C2-C10)Alkyl wherein (C2-C10)Alkyl is substituted by one or more —OH, —NRR', —OAlkyl, CF$_3$; preferably, R2' and R3' are not simultaneously H; more preferably, R2' and R3', identical or different, are independently chosen from H; Alkyl optionally substituted by one or more OH; most preferably R2'=R3'=Alkyl;

R8=H; OAlkyl; O(C2-C10)Alkyl wherein (C2-C10)Alkyl is substituted by one or more —NRR', —OH, OAlkyl, CF$_3$; a halogen atom; —NRR'; —OH; OAlkyl; CF$_3$; preferably H, —OAlkyl; more preferably OAlkyl; most preferably OMethyl;

R12=H; Alkyl optionally substituted by one or more —NRR', —OH, OAlkyl, CF$_3$,

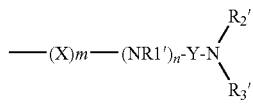

wherein X, R1', R2', R3', Y, m, n are defined as above; preferably, R12=H, Alkyl or

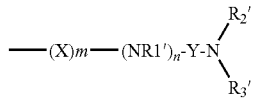

wherein X, R1', R2', R3', Y, m, n are defined as above; more preferably, R12=Alkyl;

R, R', identical or different, represent independently H, Alkyl or (C2-C10)Alkyl wherein (C2-C10)Alkyl is substituted by one or more —NRR', —OH, OAlkyl, CF$_3$;

or their acceptable salts, hydrates, or hydrated salts, or the polymorphic crystalline structures of these compounds or their optical isomers, racemates, diastereomers or enantiomers, in a suitable labelling solvent.

The one skilled in the art can readily determine the appropriate excitation or emission wavelengths for illuminating and observing the light emitted by the mixture, in order to facilitate DNA detection. These wavelengths depend on the fluorescence properties of the complex. Typically, excitation will be performed with a light source producing light at or near the wavelength of maximum absorption of the dye/nucleic acid complex. Preferably, illumination is carried out by illuminating the sample with a wavelength comprised between 400 and 450 nm, preferably 435 nm.

According to a still further preferred aspect, the emitted light can be observed after a latency period comprised between 5 sec and 1 min, preferably between 10 and 20 sec, although the exact duration may depend on various factors, including but not limited to, cell type, concentration of the compound of the invention in the medium, duration of exposure of cells to the compounds of the invention before illumination/observation, intensity of the microscope bulb, nature of fluorescence filters, nature of the objective used. Preferably, the emitted light has a wavelength comprised between 470 and 490 nm, preferably 484 nm, although which exact maximum may depend on various factors including, but not limited to, the wavelength of excitation.

Preferably, excitation wavelength is comprised between 400 and 450 nm, more preferably 435 nm, and emission wavelength is comprised between 470 and 490 nm, more preferably 484 nm.

The emission may be detected by any appropriate means, which include CCD camera, fluorometers, plate readers, fluorescence microscopes. Emission may further be detected using a flow cytometer, which makes it possible to sort portions of the sample according to their fluorescence response.

According to a still further aspect, the method for detecting DNA is quantitative and allows quantification of DNA, i.e. the emitted light is correlated with the amount of DNA in the test sample. Correlation of emitted light with the amount of DNA may be performed by comparison with light emitted by control samples (or dilutions of a control sample) of known DNA content. This may be useful for instance for real-time amplification procedures, such as real-time PCR.

According to a further object, the present invention concerns a method for determining the cell cycle stage of a test cell comprising quantifying the DNA amount by the quantitative method for labelling DNA according to the invention.

Compounds for the methods of the invention may be chosen from:

N'-(2,8-dimethoxy-12-methyl-dibenzo[c,h][1,5]naphthyridin-6-yl)-N,N-dimethyl-propane-1,3-diamine (Compound I), N'-Dibenzo[c,h][1,5]naphthyridin-6-ylmethyl-N,N-diethyl-propane-1,3-diamine (Compound 2), N'-2-[2-(Dibenzo[c,h][1,5]naphthyridin-6-ylamino)-ethylamino]-ethanol (Compound 3), N'-Dibenzo[c,h][1,5]naphthyridin-6-yl-N,N-dimethyl-ethane-1,3-diamine (Compound 4), N'-Dibenzo[c,h][1,5]naphthyridin-6-ylmethyl-N,N-dimethyl-ethane-1,3-diamine (Compound 5), N'-dibenzo[c,h][1,5]naphthyridin-6-ylmethyl-N,N-dimethyl-propane-1,2-diamine (Compound 6), N'-dibenzo[c,h][1,5]naphthyridin-6-yl-methylamino-2-methyl-propane-1,3-diol (Compound 7), N'-(2-methoxy-12-methyl-dibenzo[c,h][1,5]naphthyridin-6-yl)-N,N-dimethyl-propane-1,3-diamine (Compound 8), N6,N12-bis-(2-dimethylamino-ethyl)-2-methoxy-dibenzo[c,h][1,5]naphthyridin-6,12-diamine (Compound 9), N6,N12-bis-(3-dimethylamino-propyl)-2-methoxy-dibenzo[c,h][1,5]naphthyridine-6,12-diamine (Compound 10), N,N'-bis-(3-dimethylaminopropyl)-2,8-dimethoxy-dibenzo[c,h][1,5]naphthyridin-6,12-diamine (Compound 11), N'-(2,8-dimethoxy-12-methyl-dibenzo[c,h][1,5]naphthyridin-6-yl)-N,N-dimethyl-ethane-1,3-diamine (Compound 12), N'-(2,8-dimethoxy-dibenzo[c,h][1,5]naphthyridin-6-yl)-N,N-dimethyl-ethane-1,3-diamine (Compound 13), N,N'-bis-(3-dimethylamino-ethyl)-2,8-dimethoxy-dibenzo[c,h]-[1,5]naphthyridin-6,12-diamine (Compound 14), or their acceptable salts, hydrates, or hydrated salts, or the polymorphic crystalline structures of these compounds or their optical isomers, racemates, diastereomers or enantiomers.

According to a further object, the present invention concerns a kit for labelling DNA comprising:

a labelling solvent, as defined above, and a compound of formula (I)

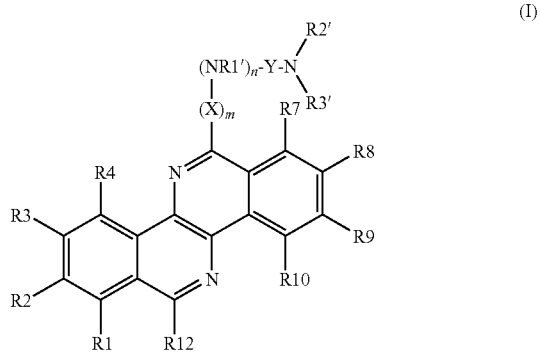

(I)

wherein

R1, R3, R4, R7, R9 and R10 are identical or different and independently chosen from H; Alkyl optionally substituted by one or more —NRR', —OH, OAlkyl, $CF_3$; a halogen atom; —NRR'; —OH; OAlkyl; $CF_3$; preferably R1=R3=R4=R7=R9=R10=H;

R2=H; OAlkyl; O(C2-C10)Alkyl wherein (C2-C10)Alkyl is substituted by one or more —NRR', —OH, OAlkyl, $CF_3$; a halogen atom; —NRR'; —OH; OAlkyl; $CF_3$; preferably H or —OAlkyl; more preferably OAlkyl;

R1'=H; Alkyl or (C2-C10)Alkyl wherein (C2-C10)Alkyl is substituted by one or more —NRR', —OH, OAlkyl, $CF_3$; a halogen atom; —NRR'; —OH; OAlkyl; $CF_3$; preferably H;

n=0 or 1; preferably, n=1;

X=linear Alkyl;

m=0 or 1; preferably, m=0;

Y=linear Alkyl; preferably, linear Alkyl comprising 3 or more carbon atoms;

R2' and R3', identical or different, are independently chosen from H; Alkyl or (C2-C10)Alkyl wherein (C2-C10)Alkyl is substituted by one or more —OH, —NRR', —OAlkyl, $CF_3$; preferably, R2' and R3' are not simultaneously H; more preferably, R2' and R3', identical or different, are independently chosen from H; Alkyl optionally substituted by one or more OH; most preferably R2'=R3'=Alkyl;

R8=H; OAlkyl; O(C2-C10)Alkyl wherein (C2-C10)Alkyl is substituted by one or more —NRR', —OH, OAlkyl, $CF_3$; a halogen atom; —NRR'; —OH; OAlkyl; $CF_3$; preferably H, —OAlkyl; more preferably OAlkyl; most preferably OMethyl;

R12=H; Alkyl optionally substituted by one or more —NRR', —OH, OAlkyl, $CF_3$,

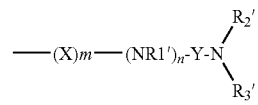

wherein X, R1', R2', R3', Y, m, n are defined as above; preferably, R12=H, Alkyl or

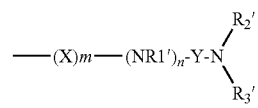

wherein X, R1', R2', R3', Y, m, n are defined as above; more preferably, R12=Alkyl;

R, R', identical or different, represent independently H, Alkyl or (C2-C10)Alkyl wherein (C2-C10)Alkyl is substituted by one or more —NRR', —OH, OAlkyl, $CF_3$;

or their acceptable salts, hydrates, or hydrated salts, or the polymorphic crystalline structures of these compounds or their optical isomers, racemates, diastereomers or enantiomers.

It will be readily apparent to the skilled in the art that the kit will contain appropriate instructions for use and reagents that depend on the assay protocol the kit is to be used for. However, the kit may optionally further include sample preparation reagents, a buffering agent, or DNA standards.

Compounds for the kit of the invention may be chosen from:
N'-(2,8-dimethoxy-12-methyl-dibenzo[c,h][1,5]naphthyridin-6-yl)-N,N-dimethyl-propane-1,3-diamine (Compound I),
N'-Dibenzo[c,h][1,5]naphthyridin-6-ylmethyl-N,N-diethyl-propane-1,3-diamine (Compound 2),
N'-2-[2-(Dibenzo[c,h][1,5]naphthyridin-6-ylamino)-ethylamino]-ethanol (Compound 3),
N'-Dibenzo[c,h][1,5]naphthyridin-6-yl-N,N-dimethyl-ethane-1,3-diamine (Compound 4),
N'-Dibenzo[c,h][1,5]naphthyridin-6-ylmethyl-N,N-dimethyl-ethane-1,3-diamine (Compound 5),
N'-dibenzo[c,h][1,5]naphthyridin-6-ylmethyl-N,N-dimethyl-propane-1,2-diamine (Compound 6),
N'-dibenzo[c,h][1,5]naphthyridin-6-yl-methylamino-2-methyl-propane-1,3-diol (Compound 7),
N'-(2-methoxy-12-methyl-dibenzo[c,h][1,5]naphthyridin-6-yl)-N,N-dimethyl-propane-1,3-diamine (Compound 8),
N6,N12-bis-(2-dimethylamino-ethyl)-2-methoxy-dibenzo[c,h][1,5]naphthyridin-6,12-diamine (Compound 9),
N6,N12-bis-(3-dimethylamino-propyl)-2-methoxy-dibenzo[c,h][1,5]naphthyridine-6,12-diamine (Compound 10),
N,N'-bis-(3-dimethylaminopropyl)-2,8-dimethoxy-dibenzo[c,h][1,5]naphthyridin-6,12-diamine (Compound 11),
N'-(2,8-dimethoxy-12-methyl-dibenzo[c,h][1,5]naphthyridin-6-yl)-N,N-dimethyl-ethane-1,3-diamine (Compound 12),
N'-(2,8-dimethoxy-dibenzo[c,h][1,5]naphthyridin-6-yl)-N,N-dimethyl-ethane-1,3-diamine (Compound 13),
N,N'-bis-(3-dimethylamino-ethyl)-2,8-dimethoxy-dibenzo[c,h][1,5]naphthyridin-6,12-diamine (Compound 14),
or their acceptable salts, hydrates, or hydrated salts, or the polymorphic crystalline structures of these compounds or their optical isomers, racemates, diastereomers or enantiomers.

The compounds of the invention are the first long wavelength non-toxic photoactivated fluorescent DNA dye reported for use as a DNA probe in cell biology.

Fluorescent Properties of the Compounds of the Invention

The absorption/emission characteristics displayed by the compounds of the invention make these compounds highly attractive as reagents for fluorescence staining of DNA. The Acridine homodimer (Ex/Em 431/498 nm) and certain low-affinity DNA-binding SYTO dyes also possess absorption/emission maxima in the same region. However, unlike the compounds of the invention, the acridine dye is cell-membrane non-permeant (Haughland et al.; Le Pecq, J. B., et al., 1975, PNAS, 72, 2915-2919) and the SYTO dyes are known to be non-selective DNA staining reagents, staining RNA in vivo, as well other structures including mitochondria (Haughland et al., supra). This is not surprising, as practically all DNA dyes also bind RNA and/or single stranded DNA (ssDNA) to some extent. For example, the thiazole orange homodimer (TOTO) and ethiduim bromide interact in vitro with ds- and ssDNA with similar affinity (Rye et al.).

The in vitro and in vivo results obtained by the inventors suggest that the compounds of the invention fluoresce preferentially when bound to double stranded DNA (dsDNA) rather than to RNA. Titration of dsDNA and RNA with the compounds of the invention showed that at low dye/base (b) or dye/base pair (bp) ratios the difference was most pronounced, with the compounds of the invention/DNA fluorescence at least 6 fold higher than that for the compounds of the invention/RNA complex. In the opposite experiment, when a fixed amount of the compounds of the invention was titrated with different amounts of dsDNA and RNA, it was also found that the compounds of the invention/dsDNA fluorescence was much higher than that for the compounds of the invention/RNA. Moreover, when the inventors titrated 5 µM the compounds of the invention with increasing amounts of DNA and RNA, they found that DNA was saturated with dye at ~30 bp/dye, while RNA could not be saturated at even a 250 b/dye ratio. On the other hand, the fact that at increasing dye/b(bp) ratios the difference in the compounds of the invention fluorescence bound to DNA or RNA was smaller (FIG. 2A) could mean that the compounds of the invention may also interact with nucleic acids through other than intercalation mechanism.

Of note, when compared to an intercalating DNA probe ethidium bromide, the compounds of the invention show surprisingly similar selectivity toward DNA over RNA. The quantum yield of the compounds of the invention when bound to DNA (13.8%) is also very close to that reported for ethidium bromide, (15%) (Le Pecq, J. B., 1971, Methods Biochem Anal, 20, 41-86). Taken together, these in vitro results indicate that at low dye/b(bp) ratios the compounds of the invention have a good selectivity for DNA over RNA. In vivo, and on fixed cells, the compounds of the invention stain only nuclei and not the cytoplasm where the bulk of RNA is localized. This suggests that the concentrations of the compounds of the invention and the conditions used for staining are optimal for efficient discrimination between dsDNA and RNA.

Interestingly, upon titration with DNA, fluorescence of the compounds of the invention increased up to a dye/bp ratio of 0.2, after which it decreased (FIG. 3B), although the length of DNA molecules continued to increase until the dye/bp ratio 1. This decrease in fluorescence is most probably due to static quenching (Lakowicz, J. R., 1991, Fluorescence Quenching: Theory and Applications. $2^{nd}$ Edn. ed. Kluwer Academic/Plenum, New York, N.Y.).

The inventors have found that the compounds of the invention fluoresce preferentially when bound to dA/dT rather than to dG/dC tracts. This differs from YO, which, when complexed with DNA, behaves in the opposite way, showing a net increase in quantum yield when complexed with dG/dC homopolymers rather than with dA/dT homopolymers (Larsson, A., et al., 1995, Biopolymers, 36, 153-167). Some other intercalators like SYBR Green I (Zipper H. et al.) and ciprofloxacin (Vilfan, I. D., et al., 2003, Biochim Biophys Acta, 1628, 111-122) display selectivity which is similar to that of the compounds of the invention. However, the difference in the fluorescence of these dyes bound to dA/dT and dG/dC homopolymers is much less pronounced than in the case of the compounds of the invention. The extent of this difference cannot be explained by the lack of binding to dG/dC tracts, as the peak of fluorescence of free compounds of the invention practically disappears as well. Also, absorption experiments show that the compounds of the invention bind similarly well to dG/dC and dA/dT tracts. All this suggests that the compounds of the invention can bind to, but interacts differently with dA/dT and dG/dC pairs of nucleotides. The observed quenching effect by dG/dC tracts could come from the low oxidation potential reported for guanine or from the electron transfer between the compounds of the invention and guanine residues as was reported for other fluorescent intercalating molecules (Vilfan, I. D. et al., supra; Larsson, A. et al., supra; Ihmels, H., et al., 2003, Org Biomol Chem, 1, 2999-3001).

Structure Function Relationship

Depending on their structure, fused poly(hetero)aromatic molecules can bind to DNA through intercalation (Lerman, L.

S. et al.), or minor/major groove binding (reviewed in Johnson, D. S. et al., 1996, In Murakami, Y. (ed.), Comprehensive Supramolecular Chemistry, Elsevier, Oxford, pp. 73-176). The compounds of the invention are neutral aza analogues of the alkaloid fagaronine (Bisagni, E., et al., supra) which is known to intercalate into DNA, but which was not reported to be a fluorescent DNA marker. The binding of the compounds of the invention to DNA is probably helped by the presence of the dialkylamine containing side chain which is positively charged at physiological pH. As was shown for other cationic dyes (Zipper, H. et al.; Blackburn, G. M. et al., 1996, Oxford University Press, Oxford, pp. 329-370; Eriksson, M., et al., 2003, *Nucleic Acids Res,* 31, 6235-6242), in vitro salt significantly affected the fluorescence of the compounds of the invention/DNA. This data support the idea that the cationic side chain participates in the binding of dye to the double-stranded helix. Hypothetically, the side chain could interact with the negative chargers on the backbone phosphate residues.

In silico docking of dyes into DNA is complicated by the fact that most of the existing docking programs only allow docking of a flexible ligand into a rigid macromolecule (DNA). An obvious limitation of such modelling is that prior to docking one has to extract from DNA an already docked molecule (in the present case Actinomycin D). This procedure leaves a space between base pairs in a rigid DNA structure, which is more or less suitable for subsequent docking of another molecule. The inventors have chosen for modelling the atomic coordinates of DNA/Actinomycin D because the portion of Actinomycin D inserted into DNA has a flat conformation, resembling that of the compound of the invention. The proposed model fits experimental data suggesting that at low dye/bp ratio the compounds of the invention can intercalate between base pairs. It is however not excluded that at higher concentrations of the compounds of the invention the dye may also show some external binding, as is the case for some other DNA probes (Zipper H. et al.). Indeed, modelling with a DNA structure without a space between base pairs (where the compounds of the invention could intercalate) suggests that the compounds of the invention could easily fit into the minor groove.

Photoactivation

In biology, two types of photoactivated fluorescent tracers are generally used: "caged" small compounds and fluorescent proteins which become "active" after illumination. Photoactivated fluorescent proteins often show little or no fluorescence when excited at the imaging wavelength, but dramatically increase their fluorescence intensity after activation by illumination at a different (usually lower) wavelength (Patterson, G. H. et al., 2002, *Science,* 297, 1873-1877). Often such activation brings about the change in the wavelength of the fluorescence emission.

Caged fluorescent compounds are non-peptide type fluorescent molecules covalently modified by the addition of a functional group that renders them non-fluorescent. Light exposure cleaves the bond to this "protecting" group, liberating the original fluorophore. The problem with caged compounds is that ultraviolet light is required to effect this reaction. To minimize cell damage by UV, the exposure time to light must be kept to the necessary minimum. The advantage of the compounds of the invention over this type of compound is that it is activated by longer wavelength light. Illumination time and DNA damage are thus not an issue.

What is the nature of the photoactivation of the compounds of the invention? As the inventors have shown, photoactivation does occur in fixed cells, indicating that the compounds of the invention did not undergo any structural modifications in vivo. Moreover, the spectra of emission of the compounds of the invention in vitro and in cells are practically identical. On the other hand, photoactivation is not observed with pure plasmid DNA. It is thus likely that this phenomenon is dependent on DNA being associated with proteins (chromatin). Indeed, both minor groove-binding probes like DAPI or intercalating molecules such as ethidium bromide or chromomycin A3 were shown to disrupt the nucleosome and/or prevent its assembly. At least, two different mechanisms may be responsible for this effect. Externally binding dyes may compete for the dA/dT rich binding sites with histones or other chromatin proteins, or inhibit DNA movement/flexibility, which is followed by reduced histone-DNA contacts within the minor groove (Fitzgerald, D. J. et al., 1999, *J Biol Chem,* 274, 27128-27138). Intercalators can unwind the DNA helix, lengthen and stiffen it (McMurray, C. T. et al., 1986, *Proc Natl Acad Sci USA,* 83, 8472-8476) and references wherein). Importantly, the inventors have shown that in vitro DNA-dependent fluorescence of the compounds of the invention is inhibited by H1. This suggests that the observed in cells photoactivation of the compounds of the invention may in fact reflect a slow binding to DNA with concomitant displacing of histones and/or other chromatin proteins from their association with DNA. This hypothesis is corroborated by the fact that, unlike in live cells, on fixed cells the compounds of the invention were immediately fluorescent, although their intensity further increased over the time. This can be explained by the fact that fixation partially denatures chromatin proteins, leaving DNA more accessible to the compound of the invention than it is the case in live cells. Finally, it remains to show why the binding of the compounds of the invention to DNA is enhanced by light.

FIGURES

FIG. 1: Compound I is a New Fluorescent DNA Dye.

A. Molecular structure and the name of compound I. B. Three-dimensional model of compound I showing a flat structure in perspective and orthogonal projections. C. Nuclei of interphase cells stained in vivo with compound I. *Xenopus* XL 177 cells were incubated in the presence of 5 µM compound I and illuminated using a standard Alexa488/FITC filter set. D. Mitotic chromosomes (anaphase) stained in vivo with compound I. E. Absorption spectra of free and DNA-bound compound I at 25 µM mixed with plasmid DNA at bp/dye ratio 8. F. Emission spectra of free and DNA-bound 1 µM compound I. Note that upon DNA binding the peak of free compound I at 438 nm decreases and shifts to 426 nm, while a new peak evolves around 472-484 nm. Plasmid DNA and dA/dT homopolymer were used at bp/dye ratio 20. In both cases, compound I was excited at 373 nm to allow the visualization of the free compound I fluorescence.

Size bar in (C) and (D)–10 µm.

Figure 2:
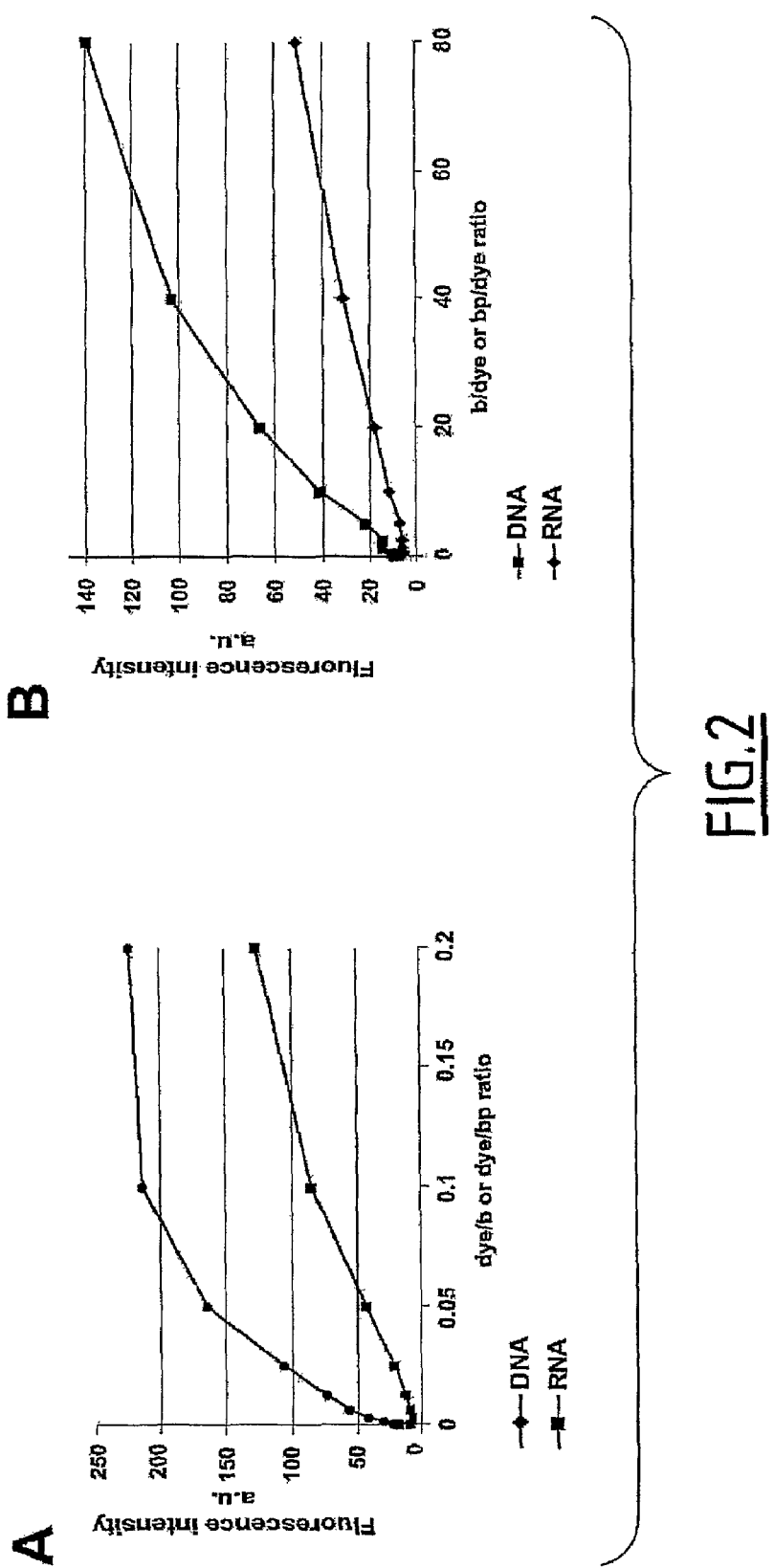

FIG. 2: Compound I Binds Preferentially to ds DNA Rather than to RNA.

A. Fluorescence emission values of different amounts of compound I mixed with 50 µM dsDNA or RNA. B. Fluorescence emission values of 1 µM compound I titrated with dsDNA and RNA.

Figure 3:
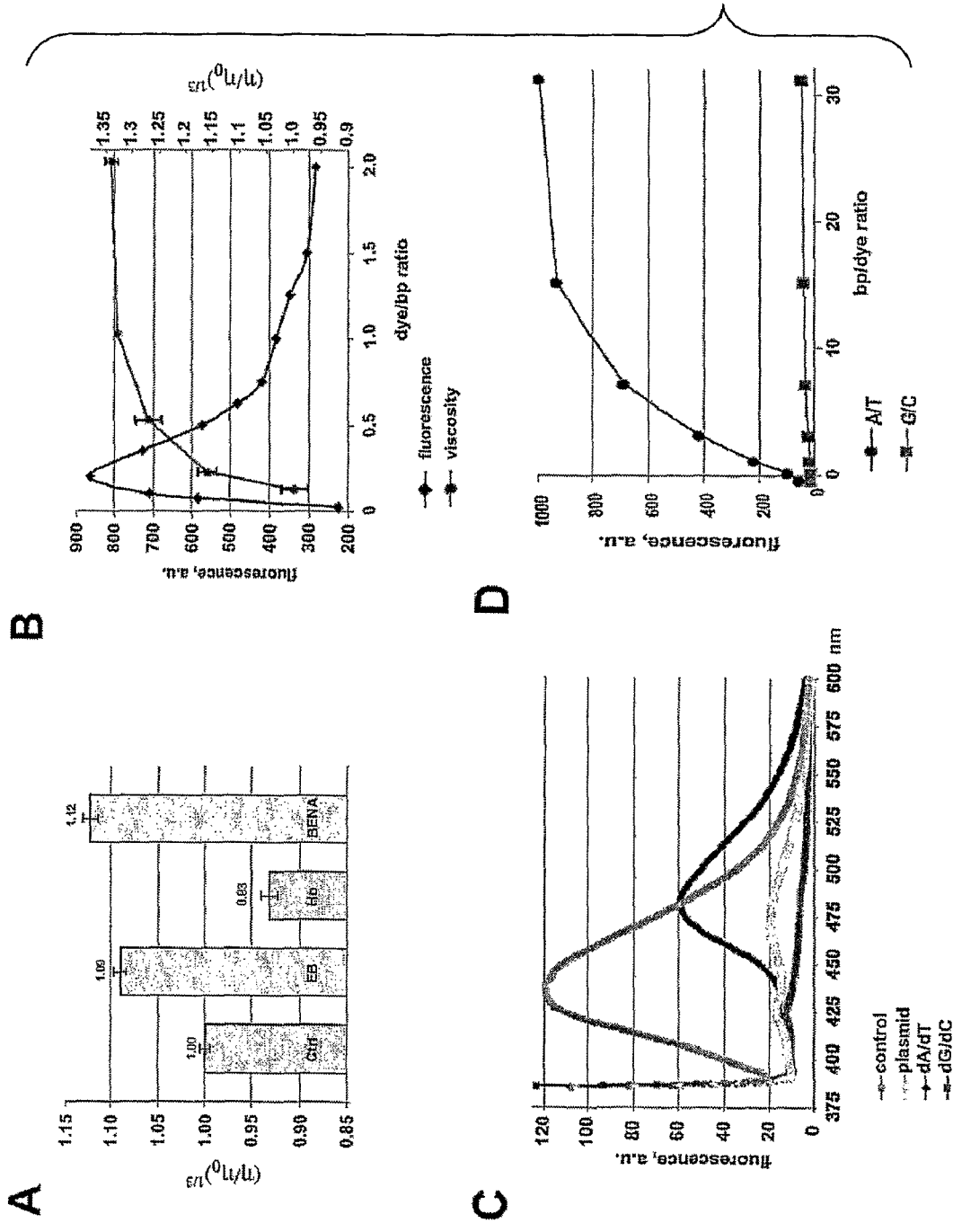

FIG. 3: Compound I Increases the Viscosity of DNA Solutions and Fluoresces Preferentially when Bound to dA/dT Rather than dG/dC DNA Tracts.

A. Relative viscosities (($\eta/\eta_0$)$^{1/3}$) of 0.5 mM CT DNA in the absence (Ctrl) or presence of different dyes at 0.1 mM concentration: ethidium bromide (EB), Hoechst 33258 (Ho) and compound I. B. Relative viscosities of CT DNA solutions in the presence of different amounts of compound I (Red curve; Y-axis on the right-hand side). Blue curve shows fluorescence intensity of the same DNA/compound I solutions used for viscosity measurements (Y-axis on the left-hand side). C. Fluorescence spectra of 1 µM compound I and 1 µM compound I mixed with plasmid DNA, dA/dT and dG/dC homopolymers taken at 40 µM. Excitation was at 373 nm to show the peak of free compound I. D. Fluorescence emission values of 5 µM compound I titrated with dA/dT and dG/dC homopolymers. Graphs show emission values at 484 nm after excitation at 435 nm.

Error bars in (A) and (B) show SEM.

Figure 4:
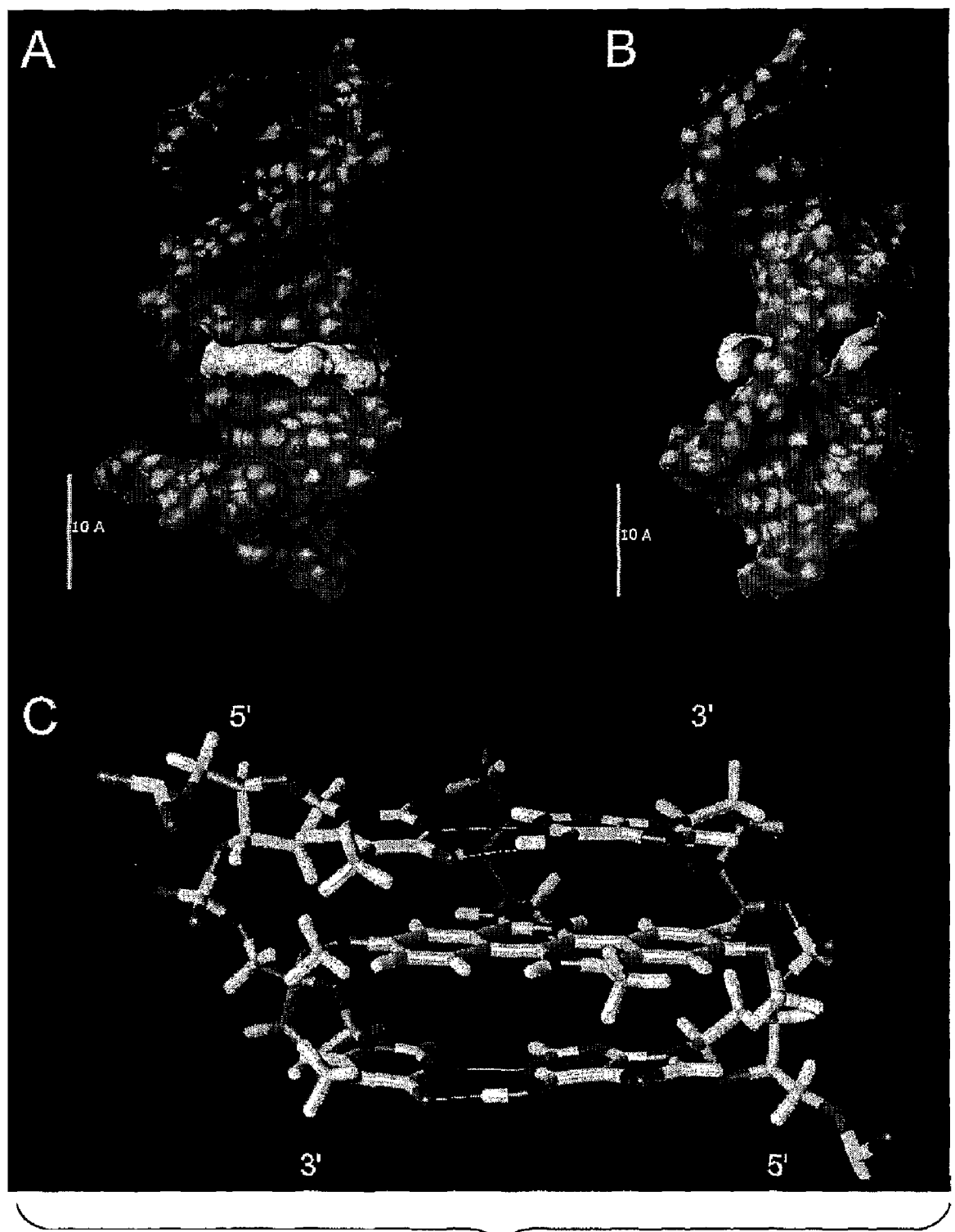

FIG. 4: Putative Model of Compound I Intercalated Between Two Pairs of dA/dT Bases.

A. View from the major groove side. B. Side view (major groove on the left hand side). C. compound I stacked between two dA/dT pairs of bases. Yellow lines represent H-bonds.

Figure 5:
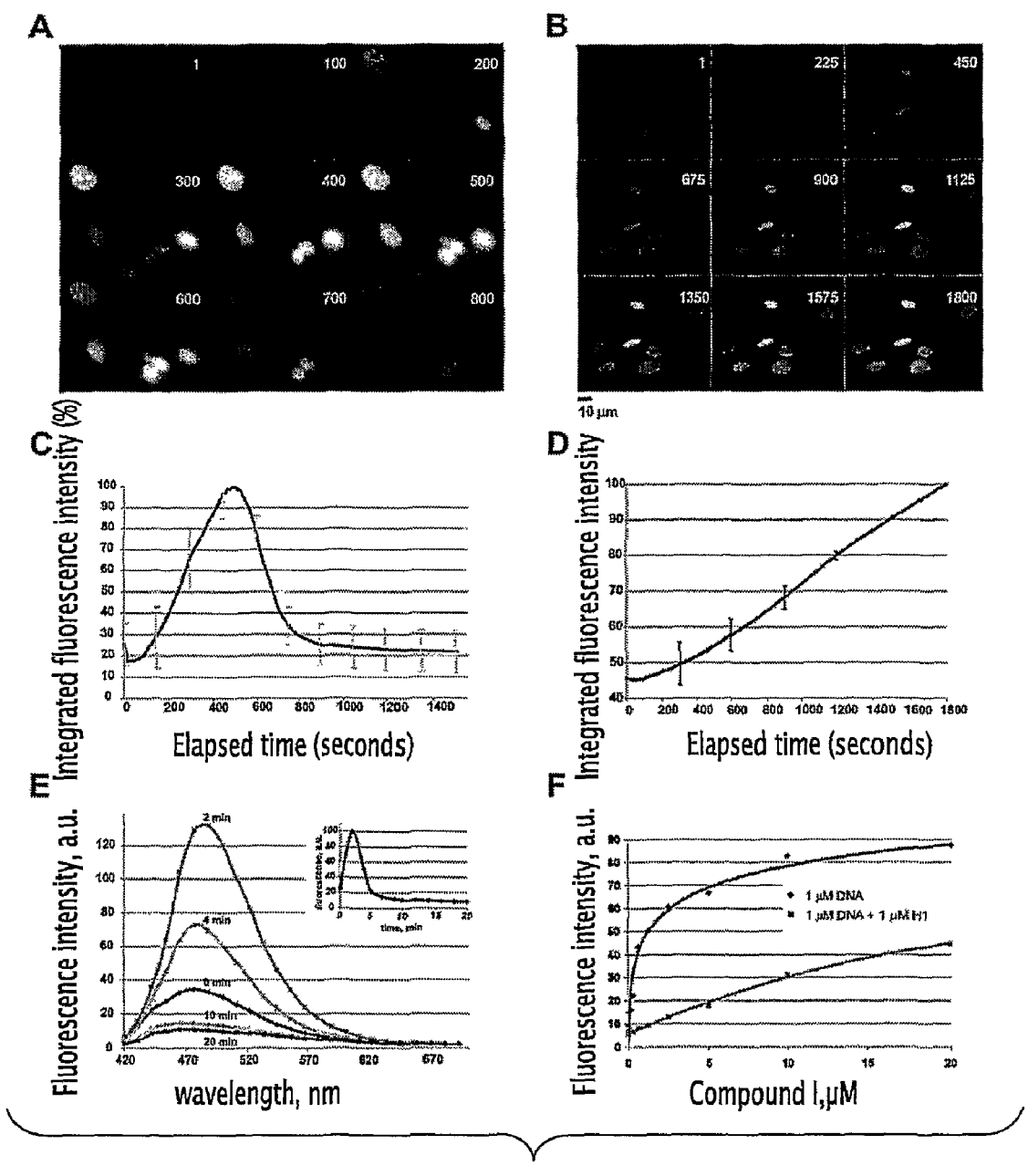

FIG. 5: Photoactivation of Compound I in Live and Fixed Cells

A. Panel of images showing photoactivation of DNA-bound compound I in live cells. Fibroblasts incubated with 5 µM compound I and illuminated using an Alexa488/FITC develop a bright nuclear signal which reaches a plateau after 8 min. Numbers correspond to time points (sec). B. Panel of images showing activation of compound I in fixed cells. Methanol-fixed primary human fibroblasts were stained with compound I as described in *Materials and Methods* and images were taken at 10 s interval during a continuous 30 min illumination using a 100 W mercury lamp. Numbers correspond to time points. In a representative nucleus average pixel values were 512 in the plane (1) and 1434 in the plane (1800). C. Quantification of the fluorescence shown in (A). Graph shows average nuclear fluorescence over 26 min. D. Quantification of the fluorescence shown in (B). Graph shows average nuclear fluorescence over 30 min. All of the nuclei shown in (B) were used for quantification. E. Representative emission spectra of the nucleus in a live 3T3 cell, incubated in the presence of 5 µM compound I and excited at 405 nm. Curves correspond to scans performed at the shown time points. Insert in the upper right corner shows activation of compound I measured in the nucleus in the course of experiment (similar to FIG. 5C). F. Fluorescence values of different amounts of compound I mixed with 1 µM plasmid DNA in the absence or presence of 1 µM histone 1. Emission at 484 nm after excitation at 435 nm. Lines were drawn through the points to guide the eye and do not represent a fitting to any equation.

Error bars in (C) and (D) correspond to standard deviation.

Figure 6:
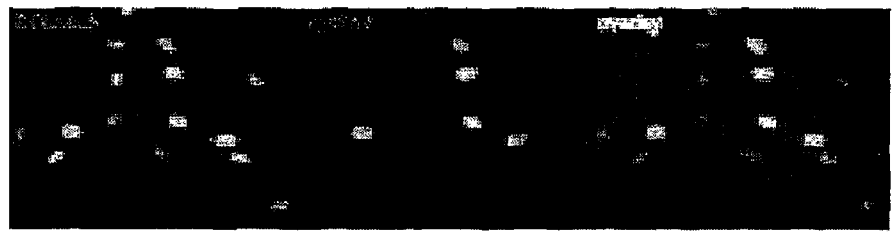
Figure 6:
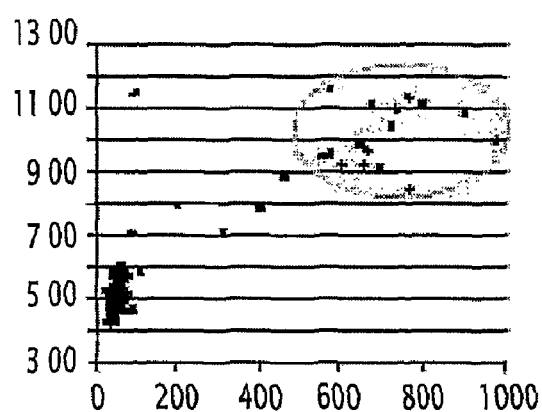

FIG. 6: Compound I Nuclear Fluorescence Reflects Cell Cycle Stage

A. Images show the same representative microscopic field with methanol-fixed fibroblasts stained using anti-cyclin A antibodies and counterstained by compound I. Images were acquired using a 20× objective. B. Quantification of the nuclear fluorescence in cells stained with compound I and anti-cyclin A antibodies (experiment shown in A). Dots represent eighty-one nuclei measured in six different randomly chosen microscopic fields. Region in the upper right corner surrounds strongly cyclin A-positive cells.

Figure 7:
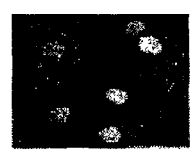
Figure 7:
Figure 7:
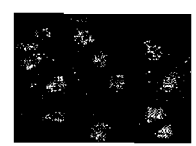
Figure 7:
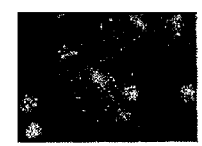
Figure 7:
Figure 7:
Figure 7:

FIG. 7: Images of the In Vivo Nuclear Staining a: Nuclear staining obtained with compound I. b: Nuclear staining obtained with compound 9. c: Nuclear staining obtained with compound 10. d: Nuclear staining obtained with compound 11. e: Nuclear staining obtained with compound 12. f: Nuclear staining obtained with compound 13. g: Nuclear staining obtained with compound 14.

The invention is further illustrated but not restricted by the description of the following examples.

EXAMPLES

A highly diverse proprietary library of 4080 compounds, corresponding to molecules synthesized by the Pharmacochemistry Laboratory at Institut Curie (UMR 176 CNRS-IC), was used as the compound set in the screening assays. This collection contains a wide variety of different heterocyclic compounds, most of which were originally prepared for a measure of their anti-cancer activity. Library components were formatted in 96 well microplates in anhydrous DMSO at 10 mM and stored at +4° C. in the dark. All manipulations were carried out taking care to protect the compounds from excessive light.

Compound I was identified in the visual phenotypic screen as a fluorescent nuclei-staining dye. Based on this result, fourteen closely related compound I-type molecules present in the compound library were studied more closely in the in vitro and in vivo tests to establish structure-function relations (Table 1). The synthesis of compound I and the related 6-amino substituted dibenzonaphthyridines 4, 12, 13 has been already described in (Bisagni, E. et al., supra). However, the entire characterization of compound I has been completed. All other new compounds were obtained as described below.

Compound I (Free base, pale yellow crystals) 88% yield, mp 162° C. (softens) to 210° C. (dec.) (Et$_2$O): 1H NMR (DMSO-d6) δ 1.95 (m, 2H, CH2-β), 2.32 (s, 6H, N(CH3)2), 2.50 (m, 2H, CH2-γ), 2.97 (s, 3H, 12-CH3), 3.76 (m, 2H, CH2-α), 3.99 & 3.96 (2*s, 2*3H, 2*OCH3), 7.45-7.60 (m, 3H, H-3+H-9+H-10), 7.75 (d, 1H, H-1, J=1.8 Hz), 7.85 (t, 1H, N—H), 8.93 (m, 2H, H-4+H-7), 9.09. Anal. (C24H28N4O2. 0.5H2O) Calcd: C, 69.71; H, 7.07; N, 13.55. Found: C, 70.01; H, 7.09; N, 13.73

Compound I

6-Methyl-dibenzo[c,h][1,5]naphthyridine

A mixture of 6-chloro-12-methyldibenzo[c,h][1,5]naphthyridine (1.10 g, 3.9 mmol) in DMF (100 mL) was hydrogenated at 100° C. under 1 atmosphere H$_2$ pressure using 10% Pd—C (300 mg) as the catalyst. Once hydrogen uptake was complete, the catalyst was removed by filtration, while the mixture was still hot, and washed with hot DMF. The filtrate was evaporated to dryness. Compound I, a yellow crystalline solid (250 mg, 28%), was obtained after silica gel column chromatography (CH$_2$Cl$_2$) and recrystallization from ethanol (mp 153° C.): $^1$H NMR (CDCl$_3$) δ 3.13 (s, 3H, CH$_3$), 7.72 (m, 2H, H-2+H-3), 7.88 (m, 2H, H-8+H-9), 8.07 (d, 1H, H-1, J=8.0 Hz), 8.21 (d, 1H, H-7, J=8.3 Hz), 9.24 (m, 2H, H-4+H-10), 9.39 (s, 1H, H-12). Anal. (C$_{17}$H$_{12}$N$_2$) Calcd: C, 83.58; H, 4.95; N, 11.47. Found: C, 83.09; H, 4.86; N, 11.40.

Compounds 2, 5, 6 and 7

(6-Aminomethyl substituted dibenzo[c,h][1,5]naphthyridine derivatives)

Step 1: SeO$_2$ oxidation: To a solution of 1 (667 mg; 3 mmol) in dioxane (90 ml) was slowly added SeO$_2$ (380 mg). The reaction mixture was refluxed for 3 h and the hot solution was then filtered and washed with hot dioxane. The solvent was removed under reduced pressure and the residue was recrystallized in toluene giving dibenzo[c,h][1,5]naphthyridine-6-carbaldehyde (450 mg, 57%), Anal. (C$_{17}$H$_{10}$N$_2$O) Calcd: C, 79.06; H, 3.90; N, 10.85. Found: C, 78.61; H, 3.77; N, 10.41.

Step 2: Reductive Amination:

N'-Dibenzo[c,h][1,5]naphthyridin-6-ylmethyl-N,N-diethyl-propane-1,3-diamine (compound 2)

Example of the General Method

NaBH$_4$ (293 mg, 7.8 mmol) was added portionwise to a refluxing solution of the above aldehyde intermediate (500 mg, 2 mmol) and N,N-diethyl-aminopropyl-1,3-diamine (620 mg, 6 mmol) in MeOH (10 mL). The mixture was refluxed for 1 h. Cold water was then added and the resulting mixture extracted with CH$_2$Cl$_2$. The combined organic layers were dried over MgSO$_4$, concentrated, and the residue was neutral alumina (7% water) column chromatographed (CH$_2$Cl$_2$/EtOH: 100/0 to 95/5 gradient). The free base of compound 2, obtained as yellow oil, was dissolved in HCl/MeOH and concentrated to dryness. Ether was added and the yellow precipitate of 2.HCl was collected (610 mg, 30%), mp 145° C. (softens) $^1$H NMR (DMSO-d$_6$) δ 1.29 (t, 6H, 2*CH$_3$), 2.43 (m, 2H, CH$_2$-β), 3.19 (m, 4H, 2*CH$_2$CH$_3$), 3.31 (m, 2H, CH$_2$-γ), 3.43 (m, 2H, CH$_2$-α), 5.29 (br s, 2H, CH$_2$-6), 8.02 (m, 2H, H-2+H-3), 8.16 (m, 2H, H-8+H-9), 8.47 (m, 2H, H-1+H-7), 9.35 (d, 1H, H-4, J=8.2 Hz), 9.54 (d, 1H, H-10, J=8.2 Hz), 9.75 (s, 1H, H-12), 10.00 (br s, 2H, H-Hydrochloride salt), 10.92 (br s, 1H, H-Hydrochloride salt). Anal (C$_{24}$H$_{29}$N$_4$.3 HCl.1.5H$_2$O) Calcd: C, 56.64; H, 6.73; N, 11.01. Found: C, 56.43; H, 6.38; N, 10.78

Using the requisite amines, compounds 6, 6 and 7 were also prepared by reductive amination.

Compound 5 (yellow powder, 56% yield) mp 160° C. (softens) 1H NMR (CDCl$_3$) δ 2.22 (s, 6H, 2*CH$_3$), 2.54 (t, 2H, CH$_2$-β J=2.9 Hz), 2.91 (m, 2H, CH$_2$-α), 4.58 (s, 2H, CH$_2$-6), 7.69 (m, 2H, H-2+H-3), 7.86 (m, 2H, H-8+H-9), 8.05 (d, 1H, H-1, J=7.8 Hz), 8.20 (d, 1H, H-7, J=8.1 Hz), 9.23 (m, 2H, H-4+H-10), 9.37 (s, 1H, H-12). Anal. (C$_{21}$H$_{22}$N$_4$.3H$_2$O) Calcd: C, 65.60; H, 7.34; N, 14.57. Found: C, 65.84; H, 6.95; N, 14.60.

Compound 6 (yellow powder, 50% yield): mp 45° C. (softens); $^1$H NMR (DMSO-d$_6$) δ 1.72 (m, 2H, CH$_2$-β), 2.15 (s, 6H, N(CH$_3$)$_2$), 2.32 (t, 2H, CH$_2$-γ), 2.82 (m, 2H, CH$_2$-α), 4.58 (s, 2H, CH$_2$-6), 7.93 (m, 2H, H-2+H-3), 8.09 (m, 2H, H-8+H-9), 8.40 (d, 1H, H-1, J=8.0 Hz), 8.59 (d, 1H, H-7, J=8.3 Hz), 9.27 (m, 2H, H-4+H-10), 9.65 (s, 1H, H-12). Anal. (C$_{22}$H$_{24}$N$_4$.3H$_2$O) Calcd: C, 66.31; H, 7.59; N, 14.06. Found: C, 66.62; H, 7.57; N, 14.12.

Compound 7 (pale pink powder, 57% yield): mp 156° C.; $^1$H NMR (CDCl$_3$) δ 1.15 (s, 3H, CH$_3$), 3.40-3.65 (m, 4H, 2*CH$_2$—OH), 4.67 (s, 2H, CH$_2$-6), 7.72 (m, 2H, H-2+H-3), 7.92 (m, 2H, H-8+H-9), 8.09 (d, 1H, H-1, J=7.8 Hz), 8.22 (d, 1H, H-7, J=7.9 Hz), 9.10 (d, 1H, H-4, J=8.4 Hz), 9.28 (d, 1H, H-10, J=8.4 Hz), 9.41 (s, 1H, H-12). Anal. (C$_{21}$H$_{23}$N$_3$O$_3$.H$_2$O) Calcd: C, 69.02; H, 6.34; N, 11.50. Found: C, 69.15; H, 6.32; N, 11.33.

Compound 3

(2-[2-(Dibenzo[c,h][1,5]naphthyridin-6-ylamino)-ethylamino]-ethanol)

6-Chloro-dibenzo[c,h][1,5]naphthyridine (500 mg, 2 mmol) was heated in 2-(2-amino-ethylamino)-ethanol (10 mL) at reflux for 3 h. Excess of diamine was evaporated to dryness under reduced pressure and the residue was extracted (CH$_2$Cl$_2$/H$_2$O). The combined organic layers were dried over MgSO$_4$, concentrated and the residue was neutral alumina (7% water) column chromatographed (EtOH—CH$_2$Cl$_2$, 0 to 10% gradient; then CH$_2$Cl$_2$/EtOH/NEt$_3$, 90/10/0.5). Compound 3 was obtained as a beige powder (65 mg, 10%), mp 100° C. (softens): 1H NMR (CDCl$_3$) δ 2.86 (t, 2H, CH$_2$CH$_2$OH, J=5.1 Hz), 3.12 (t, 2H, CH$_2$CH$_2$NHAr, J=5.7 Hz), 3.67 (t, 2H, CH$_2$NHAr, J=5.0 Hz), 3.98 (m, 2H, CH$_2$OH), 7.62 (m, 2H, H-2+H-3), 7.78 (m, 2H, H-8+H-9), 7.88 (d, 1H, H-1, J=8.1 Hz), 7.99 (d, 1H, H-7, J=8.1 Hz), 9.02 (d, H, H-4, J=8.0 Hz), 9.12 (m, 2H, H-10+H-12). Anal (C$_{20}$H$_{20}$N$_4$O.0.33H$_2$O) Calcd: C, 71.00; H, 6.11. Found: C, 71.34; H, 6.33.

Compounds 8, 9, 10, 11 and 14

(6-Dimethylaminoalkylamino- and 6,12-bis-[dimethylaminoalkylamino]-dibenzo[c,h][1,5]naphthyridines)

General Procedure

The requisite chlorointermediate [6-chloro-2-methoxy-12-methyldibenzo[c,h][1,5]naphthyridine (for 8); 6,12-dichloro-2-methoxydibenzo[c,h][1,5]naphthyridine (for 9 and 10); 6,12-dichloro-2,8-dimethoxydibenzo[c,h][1,5]naphthyridine (26) (for 11 and 14)] was heated at reflux in a large excess of either N,N-dimethylethane-1,2-diamine or N,N-dimethylpropane-1,3-diamine till disappearance of the starting chloro compound (12-48 h). The mixture was then concentrated under reduced pressure, taken up in water and extracted with CH$_2$Cl$_2$. The combined organic layers were dried over MgSO$_4$, concentrated and the residue was neutral alumina (7% water) column chromatographed (EtOH—CH$_2$Cl$_2$; 0 to 1% gradient) giving the expected 6,12-diamino substituted dibenzonaphthyridine.

Compound 8 (yellow powder, 33% yield): mp 139° C.; $^1$H NMR (CDCl$_3$) δ 1.94 (m, 2H, CH$_2$-β), 2.36 (s, 6H, N(CH$_3$)$_2$), 2.57 (t, 2H, CH$_2$-γ), 3.00 (s, 3H, 12-CH$_3$), 3.88 (m, 2H, CH$_2$-α), 3.95 (s, 3H, OCH$_3$), 7.36 (m, 2H, H-1+H-3), 7.52 (m, 1H, H-8), 7.74 (m, 3H, H-7+H-9+N—H), 9.00 (d, 1H, H-4, J=8.9 Hz), 9.09 (d, 1H, H-10, J=8.2 Hz). Anal. (C$_{23}$H$_{26}$N$_4$O) Calcd: C, 73.77; H, 7.00; N, 14.96. Found: C, 73.28; H, 6.92; N, 14.56.

Compound 9 (yellow powder, 18% yield): mp 169° C.; $^1$H NMR (DMSO-d$_6$) δ 2.29 (2*s, 2*6H, 2*N(CH$_3$)$_2$), 2.67 (m, 4H, 2*CH$_2$-β), 3.78 (m, 4H, 2*CH$_2$-α), 3.96 (s, 3H, OCH$_3$), 7.22 (m, 2H, H-8+H-9), 7.44 (dd, 1H, H-3, J=2.0 & 8.9 Hz), 7.60 (t, 1H, N—H), 7.70 (d, 1H, H-1, J=2.0 Hz), 7.78 (t, 1H, N—H), 8.24 (d, 1H, H-7, J=8.2 Hz), 8.82 (d, 1H, H-4, J=8.9

Hz), 8.88 (d, 1H, H-10, J=8.2 Hz). Anal. (C$_{25}$H$_{32}$N$_6$O.0.5H$_2$O) Calcd: C, 68.00; H, 7.53. Found: C, 68.39; H, 7.37.

Compound 10 (yellow powder, 50% yield): mp 155° C.; $^1$H NMR (DMSO-d$_6$) δ 1.96 (m, 4H, 2*CH$_2$-β), 2.24 (2*s, 2*6H, 2*N(CH$_3$)$_2$), 2.46 (m, 4H, 2*CH$_2$-γ), 3.74 (m, 4H, 2*CH$_2$-α), 3.99 (s, 3H, OCH$_3$), 7.44 (m, 3H, H-3+H-8+H-9), 7.63 (t, 1H, N—H), 7.71 (d, 1H, H-1, J=2.0 Hz), 7.81 (t, 1H, N—H), 8.29 (d, 1H, H-7, J=8.2 Hz), 8.86 (d, 1H, H-4, J=8.9 Hz), 8.95 (d, 1H, H-10, J=8.0 Hz). Anal. (C$_{27}$H$_{36}$N$_6$O) Calcd: C, 70.40; H, 7.88. Found: C, 70.03; H, 7.66.

Compound 11 (yellow powder, 70% yield): mp 216° C.; $^1$H NMR (DMSO-d$_6$) δ 1.97 (m, 4H, 2*CH$_2$-β), 2.25 (s, 12H, 2*N(CH$_3$)$_2$), 2.45 (t, 4H, 2*CH$_2$-γ), 3.73 (m, 4H, 2*CH$_2$-α), 3.98 (s, 6H, 2*OCH$_3$), 7.37 (t, 2H, 2*N—H), 7.45 (dd, 2H, H-3+H-9, J=9.0 & 2.2 Hz), 7.69 (d, 2H, H-1+H-7, J=2.2 Hz), 8.83 (d, 2H, H-4+H-10, J=9.0 Hz). Anal. (C$_{28}$H$_{38}$N$_6$O$_2$) Calcd: C, 68.54; H, 7.81; N, 17.13. Found: C, 68.35; H, 7.67; N, 17.07.

Compound 14 (yellow powder, 16% yield): mp 209° C.; $^1$H NMR (CDCl$_3$) δ 2.31 (s, 12H, 2*N(CH$_3$)$_2$, 2.73 (t, 4H, 2*CH$_2$-β), 3.84 (m, 4H, 2*CH$_2$-α), 3.93 (s, 6H, 2*OCH$_3$), 5.81 (br s, 2H, 2*N—H), 7.20 (d, 2H, H-1+H-7, J=2.3 Hz), 7.33 (dd, 2H, H-3+H-9, J=9.0 & 2.3 Hz), 8.90 (d, 2H, H-4+H-10, J=9.0 Hz). Anal. (C$_{26}$H$_{34}$N$_6$O$_2$.H$_2$O) Calcd: C, 64.98; H, 7.55. Found: C, 64.43; H, 7.41.

Stability of compound I: When stored in the dark in anhydrous DMSO at −25° C., compound I is stable for periods up to 3 years (LC-MS). When stored in DMSO at 4° C. in the dark, compound I is stable for at least one year. At ambient temperature, compound I was found to be stable in DMSO solution for at least 48 hours when stored in the dark.

Solubility of compound I: In DMSO, compound I (free base) is soluble until saturation at ~7 mM. As much as 1 volume of 7 mM, compound I in DMSO mixed with 7 volumes of H$_2$O forms a turbid solution (0.875 mM compound I in ~12% DMSO). Upon sonication for 1 min, this solution becomes limpid and can be further dissolved in aqueous solutions.

Decontamination of compound I: 2 ml of aqueous solution of compound 1 at 75 mM were incubated for 5 min at RT with 100 mg of activated charcoal. After filtration, compound I is undetectable by spectrometry.

Cell Culture and Screening

In this study, three different types of cells were used: *Xenopus* epithelial cell line XL177 (Miller, L. et al., 1977, *In Vitro*, 13, 557-563) stably transformed with a YFP-α-tubulin expressing construct (pEYFP-Tub, Clontech), mouse fibroblasts, and primary human skin fibroblasts. XL177 cells were grown at 20° C. in 60% Leibowitz-15 medium, supplemented with antibiotics, 10% fetal calf serum (FCS) and 10 mM HEPES, pH 7.2 with addition of 0.7 mg/ml G418. Cells were plated into glass-bottom 96-well plates (Greiner, Germany) and left to spread for 24 hours before being incubated in the presence of the test compounds from the Curie-CNRS small molecule library (at 25 or 50 μM final concentration) for another 20-24 hours. Mouse and human fibroblasts were grown in DMEM with antibiotics and 10% FCS at 37° C. in the presence of 5% CO$_2$. The cells were observed using a Zeiss Axiovert 200M microscope with a 40× oil immersion objective and a standard Alexa488/FITC filter (Omega, XF100-2; Ex475AF40/Em535AF45/Dichroic505). Subsequent experiments were carried out using smaller concentrations of compound I and incubation times as described in the text and figures legends. For the in vivo tests of compound I-like compounds, the molecules were added to cell culture medium at 10 μM final concentration and incubated with cells 10-60 min (up to 24 hours) prior to scoring.

Reagents

Plasmid dsDNA was purified using a Qiagen Maxiprep kit and used in the supercoiled form for absorption and fluorescence studies. *E. coli* total RNA was bought from Ambion, dA/dT and dG/dC homopolymers were purchased from Amersham Biosciences. Calf thymus (CT) high-molecular weight DNA and Hoechst 33258 were obtained from Sigma-Aldrich. Ethidium bromide was purchased from Amresco.

Spectrometry and Fluorimetry

Spectrometry and fluorimetry were performed using a SpectraMax384 (Molecular Devices) and a Luminescence Spectrometer LS50B (Perkin Elmer). Fluorescence emission of compound I in complex with DNA and RNA was measured in 50 mM Na phosphate buffer, pH 7.2 at room temperature. Before use, total *E. coli* RNA was heated to 100° C. for 1 min and immediately transferred on ice for 5 min before mixing with compound I solution. All measurements were carried out at room temperature (20-23° C.) in solutions protected from light and incubated for ~10-15 min after dilution. The units of b/dye and bp/dye are defined as moles of RNA bases or DNA base pairs per mole of dye. Quantum yield was measured using quinine sulphate as standard as described in (*Iupac Commission on Photochemistry, EPA Newsletter of November* 1986, 21-29) using FLUOROMAX-3 Spex Spectrofluorometer (HORIBA) and UVIKON XL Spectrophotometer (SECOMAM).

Viscometry

Calf thymus (CT) DNA was dissolved in 50 mM Na-phosphate buffer, pH 7.2, to a concentration of 0.1 or 0.5 mM relative to base pairs as described in the legend for FIGS. 3A and B. DNA solution was allowed to run through a custom-made capillary viscometer and the time necessary for the meniscus to pass a certain distance was measured using a stopwatch. All experiments were performed at 23° C. Viscosity values were calculated using the equation: η=(t−t$_0$)/t$_0$, where t is the flow time of DNA solution (with or without dye), and t$_0$ is the flow time of Na-phosphate buffer alone. For each control and DNA solutions with dyes flow times were measured three to five times. Viscosity of DNA solutions with dyes were calculated as (η/η$_0$)$^{1/3}$, where η$_0$ and η are relative viscosities of the CT DNA solution in the absence and presence of the dye, respectively. This calculation stems from the relationship which exists between the relative solution viscosity and the relative contour length (L/L$_0$): L/L$_0$=(η/η$_0$)$^{1/3}$, where L stands for the apparent molecular length (Muller, W. et al., 1968, *J Mol Biol*, 35, 251-290). Average viscosity values and standard error of the mean (SEM) were determined using (η/η$_0$)$^{1/3}$ values calculated for each time flow measurement.

Measuring Nuclear Fluorescence in Live Cells Stained with Compound I

Compound I at 5 μM was added directly into the cell medium 10 min before observation in an inverted microscope Zeiss Axiovert 200M with a 100 W mercury lamp. Time lapse images were acquired using CoolSnap HQ (Photometrics, Inc.) black and white camera driven by the Metamorph software (Universal Imaging). All experiments were carried out using 40× or 63× (FIGS. 1C and D) oil immersion Apochromat Zeiss objectives. To measure the fluorescence intensities, an oval region was drawn inside of each nucleus using Metamorph software and integrated intensities (nuclear surface multiplied by the average pixel value) were logged for each image.

Measuring Nuclear Fluorescence in Fixed Cells Stained with Compound I

Primary human skin fibroblasts were grown on poly-D-lysine-coated glass coverslips and fixed in cold (−20° C.) anhydrous methanol for 15 min. Samples were re-hydrated in PBS (150 mM NaCl, 20 mM Na-phosphate, pH 7.2), rinsed with 10% PBS (diluted with water) and stained with 120 µM compound I in 10% PBS for 15 min at room temperature in the dark. Samples were mounted, without washing, using the FluorSave™ mounting medium (Calbiochem) or Mowiol and analysed within 3 hours. For image acquisition (FIG. 5B,D) cells were illuminated continuously (open shutter) for 30 min using an Omega filter set XF100-2 (see above). Images were acquired at 10 sec intervals and stored in a 16-bit format as a stack. Integrated intensities of nuclear fluorescence were measured as described above and logged for each of the 180 images. Fluorescence of each region at the last time point was taken as 100% and fluorescence intensities at the same region at previous time points (frames) were calculated using Microsoft Excel software.

Spectral Analysis of Compound I Fluorescence in Live Cells

Compound I at 5 µM final concentration was added to live 3T3 mouse cells in DMEM medium just before observation using a Leica TCS-SP2 laser-scanning confocal microscope. Cellular fluorescence was observed for 20 min under continuous excitation at 405 or 458 nm using the "Lambda scanning" mode to record the emission spectra of compound I.

Molecular Modelling

The 3-dimensional atomic coordinates of compound I in pdb format were obtained using web-based software CORINA (http://www2.chemie.uni-erlangen.de/software/corina/corina.html) (Sadowski, J., 2004, In Gasteiger, J. (ed.), In Handbook of Chemoinformatics—From Data to Knowledge. Wiley-VCH, Weinheim, pp. 231-261). For computer-assisted molecular modelling the inventors employed the ArgusLab software (Thompson, M. A. (2004) ArgusLab 4.0.1. Planaria Software LLC, Seattle, Wash.) which makes use of either AScore or the Lamarckian genetic algorithm (Morris, G. M., et al., 1998, *J. Computational Chemistry*, 19, 1639-1662) scoring functions to find the low-energy binding modes. For docking of compound I into ds DNA, the inventors used 3-D molecular coordinates of a DNA dodecamer 5'-D(CpGpCpGpApApTpTp CpGpCpG)-3' (SEQ ID N°1) crystallized with an Acridine-Peptide drug intercalated in an Aa/Tt Base Step (protein data bank PDB ID-1G3X (Malinina, L., et al., 2002, *Biochemistry*, 41, 9341-9348). Prior to docking of compound I, N(α)-(9-Acridinoyl)-Tetraarginine-Amide was removed from the complex with DNA and hydrogens were added to both compound I and DNA. Molecular graphics images were produced using the UCSF Chimera package from the Resource for Biocomputing, Visualization, and Informatics at the University of California, San Francisco (Pettersen, E. F., et al., 2004, *J Comput Chem*, 25, 1605-1612).

Results

Compound I Stains Interphase Nuclei in Live Cells

During a visual phenotypic screen of the Curie-CNRS compound library on live *Xenopus* cells XL177 (using an Alexa488/FITC filter), it was found that compound I produced a bright green nuclear signal (FIG. 1C). The signal appeared after 10-20 sec illumination and was stable for many minutes thereafter (see below). The observed nuclear staining in cultured cells indicates that: (1) the drug is cell-membrane permeant; (2) non-toxic under standard cell culture conditions (up to six days in culture); (3) stains DNA or chromatin proteins or is simply accumulated in the nucleus.

Spectral Characteristics of Compound I Change Upon DNA Binding

Nuclear staining per se does not prove that a dye binds to DNA, as it could simply accumulate in the nucleus. Although compound I also stains mitotic chromosomes (FIG. 1D), theoretically it was possible that it binds specifically to DNA-associated proteins (for example histones) rather than to nucleic acids. To resolve this issue, the absorption and emission spectra of free compound I before and after addition of dsDNA were recorded. Free compound I shows a complex absorption profile with maxima at 224, 245, 283, 326, 373 and 391 nm (FIG. 1E shows the part of spectrum from 300 to 550 nm). Molar extinction coefficient (EC) of free compound I at 391 nm was measured at $10,800\ cm^{-1}\ M^{-1}$. In the presence of ds plasmid DNA the absorption peaks of compound I at 373 and 391 nm decreased, and a new peak appears with a maximum at 435 nm (FIG. 1E). An overlay of the absorption spectra in complex with dsDNA at different bp per dye ratios gives a single isosbestic point at 398 nm. Free compound I fluoresces around 438 nm (the exact position of the peak depends on the excitation wavelength). Upon DNA binding, the emission peak at 438 nm decreases and shows a hypsochromic shift to 426 nm. At the same time, a new peak evolves with a maximum around 484 nm (FIG. 1F). The exact maximum of fluorescence of compound I/DNA complexes varies insignificantly as a function of the dye/bp ratio and/or base pairs composition of the nucleic acids. For example, as shown in FIG. 1F, plasmid DNA at bp/dye ratio 40 gives a maximum at 472 nm, while in the presence of dA/dT homopolymers at the same bp/dey ratio compound I shows a maximum at 484 nm (see also below). When compound I/dsDNA solutions are excited at different wavelengths ranging from 300 nm to 500 nm, the inventors have found that although the fluorescence intensity varies considerably (with maximum found when excited at 435 nm), the emission always shows a major peak of fluorescence around 484 nm and (for shorter excitation wavelengths 323, 348, 373, 391) another shoulder at 420 nm. The quantum yield for compound I (excited at 435 nm) at 5 µM in 50 mM Na-phosphate, pH 7.2, was determined to be 2.7% for free dye and 13.8% in admixture with 50 µM CT DNA. These results show that compound I is a new DNA-binding fluorescent probe with excitation and emission in the blue/green part of the visible light spectrum.

Compound I Binds Preferentially to dsDNA Compared to RNA.

A number of known fluorescent dyes bind preferentially to dsDNA, while others, like the SYTO dyes, bind similarly well to dsDNA, ssDNA and RNA (Haugland, R. P. et al., supra). Knowing these properties is important to the design of experiments where one or another (or several) type(s) of nucleic acids may be present. To investigate the selectivity of compound I, the inventors have compared fluorescence intensities at 484 nm of the dye incubated with ds plasmid DNA or heat-denatured *E. coli* RNA. For this, DNA or RNA at 50 µM (relative to base or base pairs) was titrated with different amounts of compound I. As shown in FIG. 2A, at low dye/bp and dye/b ratios, the emission strength of compound I was significantly higher (6-fold) when mixed with DNA rather than RNA. At higher dye/b or dye/bp ratio, the difference was smaller (1.8-fold at dye/b(bp) ratio 0.2), meaning that elevated amounts of dye could saturate both types of nucleic acids. The inventors then performed the experiment in the opposite sense, i.e. titrating a fixed amount of compound I at 1 µM with increasing amounts of DNA and RNA. As demonstrated in FIG. 2B, the fluorescence of compound I mixed with dsDNA was, once again, significantly (2.5-3.6) higher compared with RNA at the same b(bp)/dye ratios. Moreover, fixed amounts of compound I could be saturated by increasing amounts of dsDNA at ~30 bp/dye ratio, but not with increasing quantities of RNA (up to 250 b/dye ratio. Taken together, these results show that compound I has a high selectivity for dsDNA over RNA and explain practically exclusively nuclear staining observed in cells (FIG. 1C).

Hydrodynamic Studies of Compound I Show that it can Intercalate Between DNA Strands.

DNA-binding dyes interact with dsDNA by intercalation or external binding, or both. External binding most often involves the minor groove of DNA (Kopka et al.; Pjura, P. E., et al., 1987, *J Mol Biol*, 197, 257-271). Intercalation occurs when a ligand inserts itself between the opposite strands of DNA. In order to determine the mechanism of compound I binding to dsDNA, the inventors performed hydrodynamic studies. This approach is based on the observation that intercalating molecules increase the length of DNA fragments and, consequently, enhance the viscosity of DNA solutions (Muller W. et al.; Suh, D. et al., 1995, *Bioorg Med Chem*, 3, 723-728). For this experiment, compound I has been compared to the known DNA intercalator ethidium bromide and to the external minor groove binder Hoechst 33258. CT DNA at 0.5 mM was mixed with drugs at 0.1 mM concentration (0.2 dye/bp ratio) and used for viscometry measurements. As shown in FIG. 3A, compound I behaves in the same way as ethidium bromide, increasing the viscosity of the DNA solution. In contrast, as previously described (Zipper, H. et al., supra), the viscosity was found to decrease slightly for Hoechst 33258.

The inventors then wondered whether the increase in viscosity is equally matched by the increase in fluorescence intensity. To answer this question, CT DNA at 0.1 mM (bp) was mixed with increasing amounts of compound I and viscosity measurements were performed as above. The viscosity of the DNA/compound I solutions increased up to a dye/bp ratio 1 (FIG. 3B). To correlate the increase in viscosity with fluorescence, the inventors measured fluorescence intensities at 484 nm of the compound I/DNA solutions used for the viscosity measurements. The maximal fluorescence intensity was reached at dye/bp ratio 0.2, after which it quickly diminished (FIG. 3B). Since the viscosity of the DNA/compound I solutions continues to increase up to the dye/bp ratio 1, the latter result suggests a "quenching" effect (Lakowicz, J. R. et al., supra). In conclusion, hydrodynamic studies show that compound I can intercalate into ds DNA.

Compound I Fluoresces Preferentially when Bound to dA/dT Rather than dG/dC DNA Tracts Many intercalating dyes and minor groove-binding DNA dyes can interact differently with dA/dT or dG/dC DNA tracts. More interestingly, even for those dyes that bind similarly well to dA/dT and dG/dC sequences, the nature of the nucleotides can affect the intensity of fluorescence (Larsson A. et al., supra). To investigate the properties of compound I when bound to different DNA tracts, the inventors examined its fluorescence in admixture with an excess of plasmid DNA and either dA/dT or dG/dC homopolymers. FIG. 3C shows that upon plasmid DNA binding compound I develops a peak at 484 nm, while the peak at 438 nm decreases significantly. The peak at 484 nm was much more pronounced when plasmid DNA was replaced by the dA/dT homopolymers (see also FIG. 1F). Surprisingly, in admixture with dG/dC homopolymer, the intensity of compound I fluorescence at 484 nm was 9.5-fold lower compared to compound I-dA/dT. This effect cannot be explained by the lack of binding to DNA, because the peak of fluorescence at 438 nm is sharply diminished (12.7-fold reduction; the peak also shifts to 426 nm). In FIG. 3C, the graphs show emission spectra upon excitation at 371 nm to allow plotting the emission of free compound I. Similar results were obtained when exciting DNA/compound I complexes at 391 and 435 nm. The inventors quantified the difference in fluorescence of compound I when bound to dA/dT and dG/dC homopolymers at different dye per base pairs ratios and found that the difference was 23-fold at dye/bp ratio 8 (FIG. 3D). Interestingly, the absorbance spectra of compound I bound to dG/dC and dA/dT homopolymers are very similar up to a dye/bp ratio 1. At higher bp/dye ratios, compound I-dG/dC absorption at 435 nm is ~30% superior than that of compound I-dA/dT, suggesting that compound I binds similarly well to both DNAs and the difference in fluorescence intensity does not reflect the lack of binding to dG/dC tracts.

Taken together, these results suggest that compound I binds similarly well to both dA/dT and dG/dC tracts but fluoresce preferentially when complexed with dA/dT sequences.

Structure-Activity Relationship in the Compound I Series

To get a further insight into how the structural properties of compound I contribute to its binding to DNA, the inventors analysed fourteen structural analogues present in the compound library. Although several of these compounds are fluorescent in vivo, this property went undetected in the initial screen most likely due to the latency period before the appearance of the signal (see below). To evaluate the activity of compound I-like molecules three tests were used: (1) in vivo, the inventors incubated human fibroblasts in the presence of the molecules and scored nuclear fluorescence in the microscope; (2 and 3) in vitro, the inventors looked at the absorption and fluorescence of free molecules before and after addition of plasmid DNA. Table 1 summarizes the results. Cells were observed in inverted epifluorescence microscope using an oil immersion objective and Alexa488/FITC filter. With the exception of compound I and analogues 8 and 12, accurate in vitro measurement of the fluorescence intensities was impossible because the emission peaks for the free molecules were too close to that for the DNA-bound dye. This affected the height of the dye/DNA peaks.

TABLE 1

Summary properties of fourteen compound I-related molecules

| Molecule | Formula MW | Structure | Absorption maxima free/DNA bound dye | Fluorescence maxima free/DNA bound dye | Images of the in vivo nuclear staining* |
|---|---|---|---|---|---|
| I | $C_{24}H_{28}N_4O_2$ 404.5 | 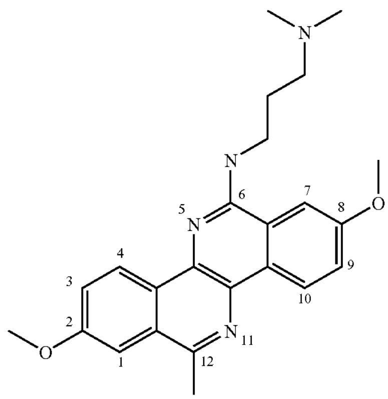 | 394/435 | 438/484 | Strong |
| 1 | $C_{17}H_{12}N_2$ 244.3 | 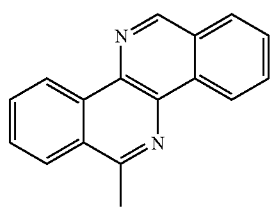 | ND/ND | ND/ND | — |
| 2 | $C_{24}H_{28}N_4$ 372.5 | 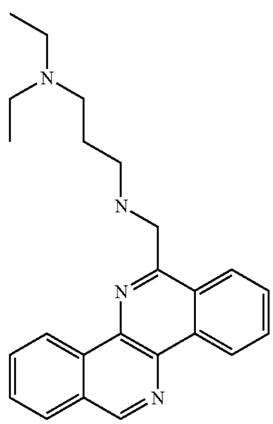 | 360/365 | ND/ND | — |
| 3 | $C_{20}H_{20}N_4O$ 332.4 | 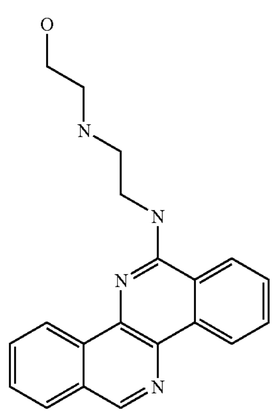 | 375/375 | ND/ND | — |

TABLE 1-continued

Summary properties of fourteen compound I-related molecules

| Molecule | Formula MW | Structure | Absorption maxima free/DNA bound dye | Fluorescence maxima free/DNA bound dye | Images of the in vivo nuclear staining* |
|---|---|---|---|---|---|
| 4 | $C_{20}H_{20}N_4$ 316.4 | 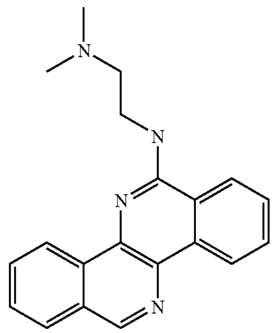 | 370/375 | 404/ND | — |
| 5 | $C_{21}H_{22}N_4$ 330.4 | 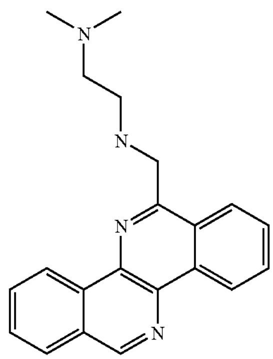 | 365/ND | 392/ND | — |
| 6 | $C_{22}H_{24}N_4$ 344.5 | 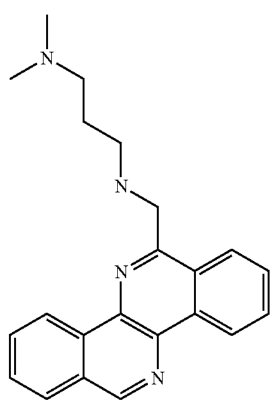 | 360/365 | 385/ND | — |
| 7 | $C_{21}H_{21}N_3O_2$ 347.4 | 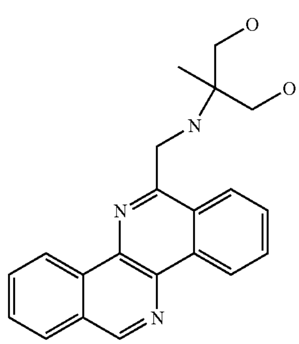 | 365/ND | ND/ND | — |

TABLE 1-continued
Summary properties of fourteen compound I-related molecules
| Molecule | Formula MW | Structure | Absorption maxima free/DNA bound dye | Fluorescence maxima free/DNA bound dye | Images of the in vivo nuclear staining* |
|---|---|---|---|---|---|
| 8 | $C_{23}H_{26}N_4O$ 374.5 | 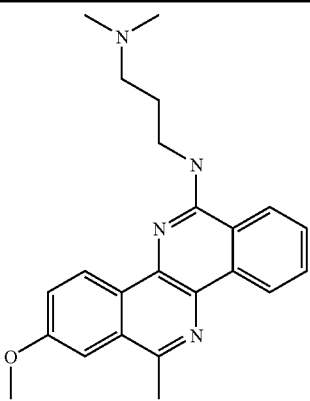 | 385/425 | 427/468 | — |
| 9 | $C_{25}H_{32}N_6O$ 432.6 | 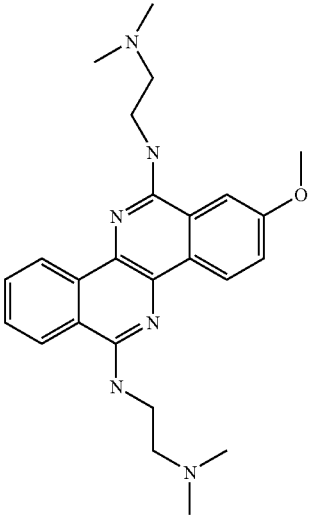 | 375/395 | 468/472 | Weak |
| 10 | $C_{27}H_{36}N_6O$ 460.6 | 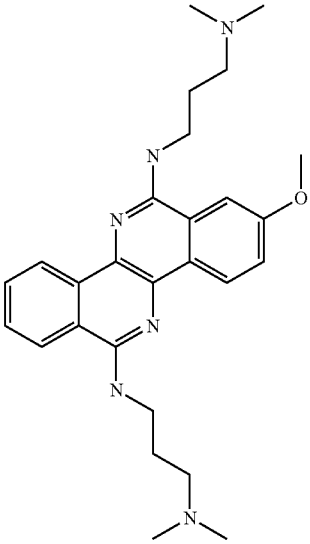 | 380/402 | 478/485 | Moderate/Strong |

TABLE 1-continued

Summary properties of fourteen compound I-related molecules

| Molecule | Formula MW | Structure | Absorption maxima free/DNA bound dye | Fluorescence maxima free/DNA bound dye | Images of the in vivo nuclear staining* |
|---|---|---|---|---|---|
| 11 | $C_{28}H_{38}N_6O_2$ 490.7 | | 390/405 | 484/500 | Moderate/Strong |
| 12 | $C_{23}H_{26}N_4O_2$ 390.5 | | 390/435 | 435/475 | Weak |
| 13 | $C_{22}H_{24}N_4O_2$ 376.5 | | 390/394 | 425/407 | Moderate[§] |

TABLE 1-continued

Summary properties of fourteen compound I-related molecules

| Molecule | Formula MW | Structure | Absorption maxima free/DNA bound dye | Fluorescence maxima free/DNA bound dye | Images of the in vivo nuclear staining* |
|---|---|---|---|---|---|
| 14 | C$_{26}$H$_{34}$N$_6$O$_2$ 462.6 | 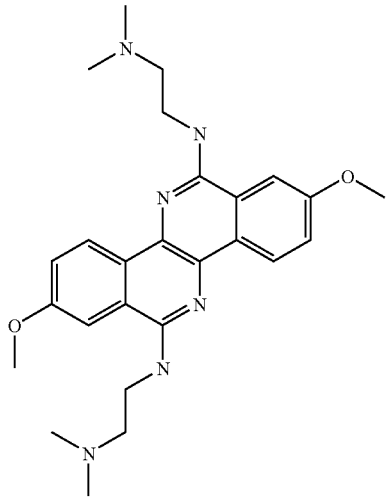 | 400/400 | 468/482 | Weak |

*Staining was defined as "weak", "moderate" or "strong" based on the nuclear signal/background ratio.
§In the presence of these molecules nuclei did not fluoresce initially when visualized in the Alexa488/FITC filter, but became noticeable after a short (10s) pre-illumination with UV light (DAPI/Hoechst filter, Omega XF03).
ND- not determined (impossible to measure).

Molecular Modelling of Compound I Binding to DNA

Modelling of compound I structure predicts a flat rigid heterocyclic core (FIG. 1B) with a flexible positively charged side chain. As hydrodynamic studies suggested that compound I intercalates between DNA strands, the inventors proposed a putative model of compound I inserted into DNA structure. For this, the inventors used the ArgusLab 4.0.1 software and the atomic coordinates of a ds DNA dodecamer 5'-D(CGCGAATTCGCG)-3' (SEQ ID N°2) complexed with an Acridine-peptide drug. For docking, the inventors used the ArgusLab scoring function AScore and a grid encompassing the whole dodecamer. The lowest energy conformation (−4.00 kcal/mol), shown in FIG. 4, represents compound I stacked between two pairs of nucleotides (AT/AT). Similar results were obtained using a genetic algorithm scoring function or two pairs of GC nucleotides.

Compound I is Activated by Light

Original in vivo observations of compound I-treated cells showed that the green nuclear staining appeared after a latency period of 10-20 seconds (depending on concentration), suggesting a photoactivation phenomenon. To quantify this effect, live mouse fibroblasts were incubated in the presence of 5 μM compound I and time-lapse video microscopy was used to film the cells. Nuclear fluorescence develops slowly in the nuclei of cells treated with compound I and illuminated continuously using a standard Alexa488/FITC filter set (475AF40, 535AF45) (FIG. 5A). Fluorescence peaked after 8 min of illumination and then started to fade (FIG. 5C), most likely reflecting the "bleaching" of compound I. The photoactivation concerned only the cells in the illuminated field, as nuclei of cells immediately outside of the illuminated field remained imperceptible (non-fluorescent).

Theoretically, it was possible that photoactivation was due to a chemical modification of the structure of compound I catalyzed by living cells. To test this possibility, the inventors stained nuclei of fixed cells with compound I and measured nuclear fluorescence during a continuous 30 min illumination. FIGS. 5B and D show that in fixed cells compound I/DNA fluorescence increase linearly over a long period of time. Nuclei of cells located immediately outside of the illuminated field remained dim. Photoactivation did not happen when compound I was mixed with DNA at different dye/bp ratios and illuminated in the microscope as described above. Theoretically, it was possible that the increase in fluorescence as seen in a band pass Alexa488/FITC filter represented a shift in the wavelength of emission over time. To determine whether this was occurring, the inventors recorded spectra of compound I emission in the nuclei of live cells using a confocal microscope. FIG. 5E shows that the emission spectrum of DNA-bound compound I does not change considerably over time when excited at 405 nm. Similar results were obtained using excitation at 458 nm, meaning that the change in fluorescence intensities does not result from a major change in the emission wavelength.

As competition with chromatin proteins such as histones and HGM1 has been shown to affect binding of both external binders (Fitzgerald D. J. et al.; Churchill, M. E. et al., 1989, Embo J, 8, 4189-4195; Reeves, R. et al., 1990, J Biol Chem, 265, 8573-8582) and intercalating small molecules (McMurray, C. T., et al., 1991, Biochemistry, 30, 5644-5652; Mir, M. A. et al., 2001, Biochemistry, 40, 11578-11585; Mir, M. A., et al., 2004, Biophys Chem, 109, 121-135), the inventors wondered whether compound I/DNA fluorescence was affected by the presence of histones. Titration of 1 μM plasmid DNA with compound I in the absence or presence of 1 μM human histone 1 (H1) showed that H1 significantly affected the fluorescence of compound I (FIG. 5F). At the same time, free compound I fluorescence (excited at 391 nm) was not quenched by H1.

The inventors concluded therefore that compound I fluorescence in cells is activated by light, and this photoactivation most likely depends on DNA being in complex with proteins which are not affected by methanol fixation.

Compound I Allows an Easy DNA Quantification in Cells

Some of the compound I-stained nuclei appeared brighter than others (FIG. 1C and FIG. 5A, B) suggesting that fluorescence intensities may be proportional to their DNA content and correspondingly reflect their cell cycle status, as was shown for other DNA probes, for example for PicoGreen and SYBR Green I. Probing directly DNA content in live cells already stained by compound I would necessitate using another dsDNA-binding dye. Such a double staining carried the risk of a possible competition for binding sites and/or unpredictable effects on fluorescence. Therefore, the inventors decided to compare the integrated total fluorescence of compound I-stained nuclei in fixed cells with a known cell cycle protein marker. The inventors fixed primary human fibroblasts with methanol, performed indirect immunofluorescence with anti-cyclin A antibodies, followed by Alexa 568-labelled secondary antibodies and counterstained nuclei with compound I. Cyclin A accumulates in cells beginning at the S phase and throughout the G2 cell cycle phase, and unlike cyclin B, is practically all nuclear (rev. in Pines, J. et al., 1992, *Ciba Found Symp*, 170, 187-196; discussion 196-204.). This fact facilitates the correlation of compound I/DNA fluorescence with that of cyclin A. Indeed, the inventors found that cells negative for cyclin A have significantly lower compound I fluorescence in the nucleus (FIG. 6A). Moreover, the inventors observed a direct correlation of the compound I fluorescence with that of cyclin A in cyclin A-positive cells (FIG. 6B). Of note is that strongly cyclin A-positive nuclei (FIG. 6B, dots in the upper right corner showed by oval) contain approximately twice as much compound I-fluorescence as cyclin A-negative nuclei. This correlates well with 2N and 4N DNA content expected to be found in G1 and G2 cells, respectively. These results show that compound I allows an easy quantification of nuclear DNA content, reflecting the cell cycle stage.

The invention claimed is:

1. A compound of formula (I)

(I)

wherein:

R1, R3, R4, R7, R9 and R10 are identical or different and independently chosen from H; Alkyl optionally substituted by one or more —NRR', —OH, OAlkyl, $CF_3$; a halogen atom;

R2=H; OAlkyl; O(C2-C10)Alkyl wherein (C2-C10)Alkyl is substituted by one or more —NRR', —OH, OAlkyl, $CF_3$; a halogen atom;

R1'=H; Alkyl or (C2-C10)Alkyl wherein (C2-C10)Alkyl is substituted by one or more —NRR', —OH, OAlkyl, $CF_3$; a halogen atom;

n=0 or 1;

X=linear Alkyl;

m=0 or 1;

Y=linear Alkyl;

R2' and R3', identical or different, are independently chosen from H; Alkyl or (C2-C10)Alkyl wherein (C2-C10) Alkyl is substituted by one or more —OH, —NRR', —OAlkyl, $CF_3$;

R8=H; OAlkyl; O(C2-C10)Alkyl wherein (C2-C10)Alkyl is substituted by one or more —NRR', —OH, OAlkyl, $CF_3$; a halogen atom;

R12=H; Alkyl optionally substituted by one or more —NRR', —OH, OAlkyl, $CF_3$,

—(X)m—(NR1')n-Y-N(R2')(R3')

wherein X, R1', R2', R3', Y, m, n are defined as above;

R, R', identical or different, represent independently H, Alkyl or (C2-C10)Alkyl wherein (C2-C10)Alkyl is substituted by one or more —NRR', —OH, OAlkyl, $CF_3$; or their acceptable salts, hydrates, or hydrated salts, or the polymorphic crystalline structures of these compounds or their optical isomers, racemates, diastereomers or enantiomers, with the exception of compounds wherein:

R1=R3=R4=R7=R9=R10=H, m=0, n=1, R1'=H, R2'=R3'=Methyl, R2, R8 represent independently H or OMethyl, R12=H or Methyl and Y=—$(CH_2)_2$— or —$(CH_2)_3$—.

2. A compound according to claim 1, wherein

R1=R4=R7=R9=R10=H;

R2=H or —OAlkyl;

R1'=H;

n=0 or 1;

X=linear Alkyl;

m=0 or 1;

Y=linear Alkyl;

R2' and R3' identical or different, are independently chosen from H; Alkyl or (C2-C10)Alkyl substituted by one or more OH, and are not simultaneously H;

R8=H, OAlkyl;

R12=H, Alkyl or

—(X)m—(NR1')n-Y-N(R2')(R3')

wherein X, R1', R2', R3', Y, m, n are defined as in claim 1

R, R', identical or different, represent independently H, Alkyl or (C2-C10)Alkyl substituted by one or more —NRR', —OH, OAlkyl, CF$_3$, or their acceptable salts, hydrates, or hydrated salts, or the polymorphic crystalline structures of these compounds or their optical isomers, racemates, diastereomers or enantiomers, with the exception of compounds wherein:

R1=R3=R4=R7=R9=R10=H, m=0, n=1, R1'=H, R2'=R3'=Methyl, R2, R8 represent independently H or OMethyl, R12=H or Methyl and Y=—(CH$_2$)$_2$— or —(CH$_2$)$_3$—.

3. A compound according to claim 1 selected from:

N'-Dibenzo[c,h][1,5]naphthyridin-6-ylmethyl-N,N-diethyl-propane-1,3-diamine,

2-[2-(Dibenzo[c,h][1,5]naphthyridin-6-ylamino)-ethylamino]-ethanol, dibenzo[c,h][1,5]naphthyridin-6-yl-methyl-N,N-dimethyl-ethane-1,2-diamine, N'-dibenzo[c,h][1,5]naphthyridin-6-yl-methyl-N,N-dimethyl-propane-1,3-diamine, N'-dibenzo[c,h][1,5]naphthyridin-6-yl-methylamino-2-methyl-propane-1,3-diol, N'-(2-methoxy-12-methyl-dibenzo[c,h][1,5]naphthyridin-6-yl)-N,N-dimethyl-propane-1,3-diamine, N6,N12-bis-(2-dimethylamino-ethyl)-2-methoxy-dibenzo[c,h][1,5]naphthyridin-6,12-diamine, N6,N12-bis-(3-dimethylamino-propyl)-2-methoxy-dibenzo[c,h][1,5]naphthyridine-6,12-diamine, N,N'-bis-(3-dimethylaminopropyl)-2,8-dimethoxy-dibenzo[c,h][1,5]naphthyridin-6,12-diamine, N,N'-bis-(3-dimethylamino-ethyl)-2,8-dimethoxy-dibenzo[c,h][1,5]naphthyridin-6,12-diamine, or their acceptable salts, hydrates, or hydrated salts, or the polymorphic crystalline structures of these compounds or their optical isomers, racemates, diastereomers or enantiomers.

4. A method of using a compound of formula (I) as a DNA probe, comprising:

contacting DNA with the compound of formula (I):

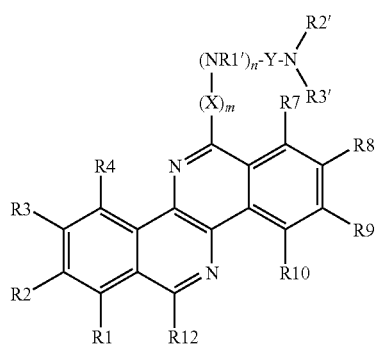

(I)

wherein:

R1, R3, R4, R7, R9 and R10 are identical or different and independently chosen from H;

Alkyl optionally substituted by one or more —NRR', —OH, OAlkyl, CF$_3$; a halogen atom;

R2=H; OAlkyl; O(C2-C10)Alkyl wherein (C2-C10)Alkyl is substituted by one or more —NRR', —OH, OAlkyl, CF$_3$; a halogen atom;

R1'=H; Alkyl or (C2-C10)Alkyl wherein (C2-C10)Alkyl is substituted by one or more —NRR', —OH, OAlkyl, CF$_3$; a halogen atom;

n=0 or 1;

X=linear Alkyl;

m=0 or 1;

Y=linear Alkyl;

R2' and R3', identical or different, are independently chosen from H; Alkyl or (C2-C10)Alkyl wherein (C2-C10)Alkyl is substituted by one or more —OH, —NRR', —OAlkyl, CF$_3$;

R8=H; OAlkyl; O(C2-C10)Alkyl wherein (C2-C10)Alkyl is substituted by one or more —NRR', —OH, OAlkyl, CF$_3$; a halogen atom;

R12=H; Alkyl optionally substituted by one or more —NRR', —OH, OAlkyl, CF$_3$,

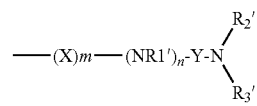

wherein X, R1', R2', R3', Y, m, n are defined as above;

R, R', identical or different, represent independently H, Alkyl or (C2-C10)Alkyl wherein (C2-C10)Alkyl is substituted by one or more —NRR', —OH, OAlkyl, CF$_3$;

or their acceptable salts, hydrates, or hydrated salts, or the polymorphic crystalline structures of these compounds or their optical isomers, racemates, diastereomers or enantiomers and detecting complexes formed between the compound of formula (I) and the DNA.

5. A DNA labelling solution comprising a compound of formula (I)

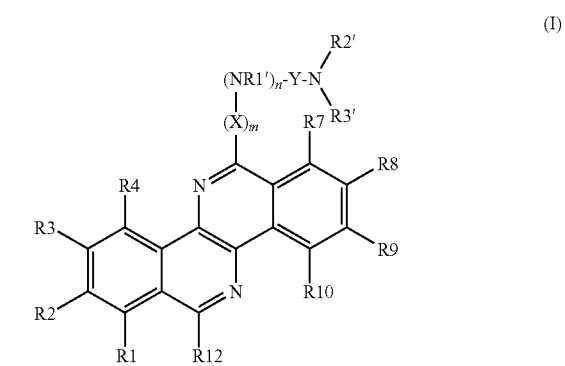

(I)

as defined in claim 4 or their acceptable salts, hydrates, or hydrated salts, or the polymorphic crystalline structures of these compounds or their optical isomers, racemates, diastereomers or enantiomers, in a suitable labelling solvent.

6. An in vivo and/or in vitro method for detecting DNA in a test sample which comprises the steps consisting of:
a) contacting a test sample with a derivative of formula (I)

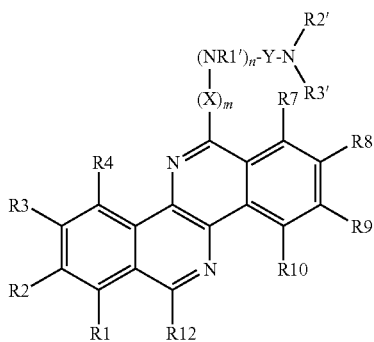

(I)

as defined in claim 4
or their acceptable salts, hydrates, or hydrated salts, or the polymorphic crystalline structures of these compounds or their optical isomers, racemates, diastereomers or enantiomers;
b) incubating the mixture resulting from the contacting of the test sample and derivative of formula (I), for a time and under conditions sufficient for the derivative of formula (I) to form a complex with a DNA likely to be present in the test sample;
c) illuminating the mixture with an appropriate wavelength and observing the light emitted by the illuminated mixture, whereby the DNA is detected.

7. The method according to claim 6, which is quantitative and wherein the light emitted by the illuminated mixture is correlated with the amount of DNA in the test sample.

8. The method according to claim 6, wherein the test sample is a biological sample.

9. The method according to claim 8, wherein the test sample is selected from the group consisting of urine, sera, blood, plasma, cerebrospinal fluid, saliva, tear fluid, mucus, tissues optionally fixed or immobilized, eukaryotic or prokaryotic cells optionally fixed or immobilized, a cell lysate, microorganism an electrophoretic matrix or polymeric gel, or a buffered solution.

10. The method according to claim 6, wherein the DNA is synthetic DNA.

11. The method according to claim 6, wherein the compound of formula (I) chosen from:
N'-(2,8-dimethoxy-12-methyl-dibenzo[c,h][1,5]naphthyridin-6-yl)-N,N-dimethyl-propane-1,3-diamine,
N'-Dibenzo[c,h][1,5]naphthyridin-6-ylmethyl-N,N-diethyl-propane-1,3-diamine,
2-[2-(Dibenzo[c,h][1,5]naphthyridin-6-y)amino)-ethylamino]-ethanol,
N'-Dibenzo[c,h][1,5]naphthyridin-6-yl-N,N-dimethyl-ethane-1,3-diamine,
N'-Dibenzo[c,h][1,5]naphthyridin-6-ylmethyl-N,N-dimethyl-ethane-1,3-diamine,
N'-dibenzo[c,h][1,5]naphthyridin-6-ylmethyl-N,N-dimethyl-propane-1,2-diamine,
N'-dibenzo[c,h][1,5]naphthyridin-6-yl-methylamino-2-methyl-propane-1,3-diol,
N'-(2-methoxy-12-methyl-dibenzo[c,h][1,5]naphthyridin-6-yl)-N,N-dimethyl-propane-1,3-diamine,
N6,N12-bis-(2-dimethylamino-ethyl)-2-methoxy-dibenzo[c,h][1,5]naphthyridin-6,12-diamine,
N6,N12-bis-(3-dimethylamino-propyl)-2-methoxy-dibenzo[c,h][1,5]naphthyridine-6,12-diamine,
N,N'-bis-(3-dimethylaminopropyl)-2,8-dimethoxy-dibenzo[c,h][1,5]naphthyridin-6,12-diamine,
N-(2,8-dimethoxy-12-methyl-dibenzo[c,h][1,5]naphthyridin-6-yl)-N,N-dimethyl-ethane-1,3-diamine,
N[I]-(2,8-dimethoxy-dibenzo[c,h][1,5]naphthyridin-6-yl)-N,N-dimethyl-ethane-1,3-diamine,
N,N'-bis-(3-dimethylamino-ethyl)-2,8-dimethoxy-dibenzo[c,h][1,5]naphthyridin-6,12-diami[pi]e,
or their acceptable salts, hydrates, or hydrated salts, or the polymorphic crystalline structures of these compounds or their optical isomers, racemates, diastereomers or enantiomers.

12. A kit for labelling DNA comprising:
a labelling solvent, and
a compound of formula (I)

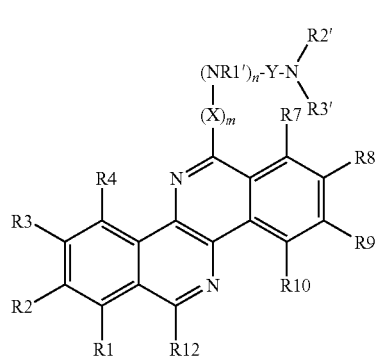

(I)

as defined in claim 4,
or their acceptable salts, hydrates, or hydrated salts, or the polymorphic crystalline structures of these compounds or their optical isomers, racemates, diastereomers or enantiomers.

13. The kit according to claim 12, wherein the labelling solvent selected from the group consisting of an aqueous solvent, a buffer solution, and an organic solvent.

14. The kit according to claim 12, wherein the labelling solvent further comprises a detergent and/or stabilizer.

* * * * *

UNITED STATES PATENT AND TRADEMARK OFFICE
CERTIFICATE OF CORRECTION

PATENT NO. : 7,728,128 B2
APPLICATION NO. : 12/280715
DATED : June 1, 2010
INVENTOR(S) : Popov et al.

It is certified that error appears in the above-identified patent and that said Letters Patent is hereby corrected as shown below:

On Title page Item (73) Assignees:

Please change "Institut National de la Sante et de la Recherche Medicate (INSERM), Paris (FR); Institute Curie, Paris (FR); Centre National de la Recherche Scientifique (C.N.R.S.), Paris (FR); Commissariat a l'Energie Atomique, Paris (FR)" to -- Institut National de la Sante et de la Recherche Medicale (INSERM), Paris (FR); Institute Curie, Paris (FR); Centre National de la Recherche Scientifique (C.N.R.S.), Paris (FR); Commissariat a l'Energie Atomique, Paris (FR) --

Signed and Sealed this

Fifth Day of October, 2010

David J. Kappos
*Director of the United States Patent and Trademark Office*